US012569248B2

(12) United States Patent
Patel et al.

(10) Patent No.: US 12,569,248 B2
(45) Date of Patent: Mar. 10, 2026

(54) ORTHOPEDIC STAPLE AND RELATED INSTRUMENTS

(71) Applicant: WRIGHT MEDICAL TECHNOLOGY, INC., Memphis, TN (US)

(72) Inventors: Vinay D. Patel, Memphis, TN (US); George Matthew Awtrey, Bartlett, TN (US); Robert Michael Carlo, III, Lakeland, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 0 days.

(21) Appl. No.: 18/413,197

(22) Filed: Jan. 16, 2024

(65) Prior Publication Data

US 2024/0148378 A1     May 9, 2024

Related U.S. Application Data

(62) Division of application No. 17/840,673, filed on Jun. 15, 2022, now abandoned.

(51) Int. Cl.
*A61B 17/076*          (2006.01)
*A61B 17/064*          (2006.01)
(Continued)

(52) U.S. Cl.
CPC ........ *A61B 17/076* (2013.01); *A61B 17/0642* (2013.01); *A61B 2017/0641* (2013.01);
(Continued)

(58) Field of Classification Search
CPC ............ A61B 17/0644; A61B 17/8875; A61B 17/076; A61B 17/068; A61B 17/1728;
(Continued)

(56) References Cited

U.S. PATENT DOCUMENTS 5,584,839 A     12/1996  Gieringer
D705,930 S  *   5/2014  Cheney ........................ D24/145
(Continued)

FOREIGN PATENT DOCUMENTS

FR          3023468 B1     6/2019
GB          2471648 B      1/2012
(Continued)

OTHER PUBLICATIONS

Extended European Search Report issued in connection with corresponding European Patent Application No. 21781556.2, Jun. 5, 2024, 15 pages.
(Continued)

*Primary Examiner* — Marcela I. Shirsat
(74) *Attorney, Agent, or Firm* — DUANE MORRIS LLP

(57)          ABSTRACT

A method to remove a memory metal orthopedic staple from that is implanted in a bone repair site is disclosed. The orthopedic staple is in its relaxed state and the method includes (a) attaching an inserter tool/cartridge assembly to the orthopedic staple's bridge portion; (b) actuating the inserter tool to change the orthopedic staple from its relaxed state to its insertion state in which the two legs of the orthopedic staple are substantially parallel to each other; and (c) removing the orthopedic staple from the bone repair site.

8 Claims, 25 Drawing Sheets

(Cartridge Receiving Position)

(51) Int. Cl.

| | |
|---|---|
| *A61B 17/068* | (2006.01) |
| *A61B 17/072* | (2006.01) |
| *A61B 17/10* | (2006.01) |
| *A61B 17/17* | (2006.01) |
| *A61F 2/08* | (2006.01) |

(52) U.S. Cl.
CPC ... *A61B 17/0644* (2013.01); *A61B 2017/0645* (2013.01); *A61B 2017/0646* (2013.01); *A61B 17/068* (2013.01); *A61B 2017/0688* (2013.01); *A61B 2017/07214* (2013.01); *A61B 2017/07264* (2013.01); *A61B 17/10* (2013.01); *A61B 17/1714* (2013.01); *A61F 2/0811* (2013.01); *Y10S 411/92* (2013.01)

(58) Field of Classification Search
CPC ..... A61B 17/1714; A61B 17/17; A61B 17/10; A61B 17/0642; A61B 2017/0645; A61B 2017/0641; A61B 2017/0646; A61B 2017/564; A61B 2017/0688; A61B 2017/07214; A61B 2017/07264; A61F 2/0811; Y10S 411/92
USPC .......................................................... 606/75
See application file for complete search history.

(56) References Cited

U.S. PATENT DOCUMENTS

| | | | | |
|---|---|---|---|---|
| D777,329 | S | * | 1/2017 | Montoya ...................... D24/155 |
| 9,820,759 | B1 | | 11/2017 | Scott et al. |
| 10,117,647 | B2 | | 11/2018 | Cheney |
| 10,307,156 | B1 | * | 6/2019 | Blair .................. A61B 17/0642 |
| 2009/0228006 | A1 | | 9/2009 | Mussolin |
| 2010/0125275 | A1 | * | 5/2010 | Kinmon ............. A61B 17/1739 |
| | | | | 606/103 |
| 2010/0152745 | A1 | | 6/2010 | Dudasik et al. |
| 2010/0237128 | A1 | * | 9/2010 | Miller ................ A61B 17/0682 |
| | | | | 227/175.1 |
| 2011/0060338 | A1 | | 3/2011 | Kim |
| 2013/0213843 | A1 | * | 8/2013 | Knight ................... A61B 50/30 |
| | | | | 434/262 |
| 2014/0018809 | A1 | | 1/2014 | Allen |
| 2014/0031828 | A1 | | 1/2014 | Patel et al. |
| 2014/0277516 | A1 | | 9/2014 | Miller et al. |
| 2016/0074037 | A1 | | 3/2016 | Cheney et al. |
| 2016/0235460 | A1 | | 8/2016 | Wahl |
| 2017/0065275 | A1 | * | 3/2017 | Cheney ................ A61B 17/064 |
| 2017/0181840 | A1 | | 6/2017 | Floess et al. |
| 2017/0231625 | A1 | * | 8/2017 | Handie .................. A61B 17/10 |
| | | | | 227/175.1 |
| 2017/0281157 | A1 | | 10/2017 | Hartdegen et al. |
| 2017/0296174 | A1 | | 10/2017 | Wahl et al. |
| 2018/0271521 | A1 | * | 9/2018 | Wahl .................. A61B 17/0682 |
| 2020/0000464 | A1 | | 1/2020 | Gaston et al. |
| 2020/0000465 | A1 | | 1/2020 | Maclure et al. |
| 2021/0298748 | A1 | | 9/2021 | Campbell et al. |

FOREIGN PATENT DOCUMENTS

| | | | |
|---|---|---|---|
| WO | 2014160024 | A1 | 10/2014 |
| WO | 2017011589 | A1 | 1/2017 |

OTHER PUBLICATIONS

Partial European Search Report issued in connection with corresponding European Patent Application No. 21781556.2, Mar. 7, 2024, 11 pages.

International Search Report and Written Opinion issued in connection with International Patent Application No. PCT/US2021/018330, Jul. 1, 2021, 19 pages.

* cited by examiner

100

300

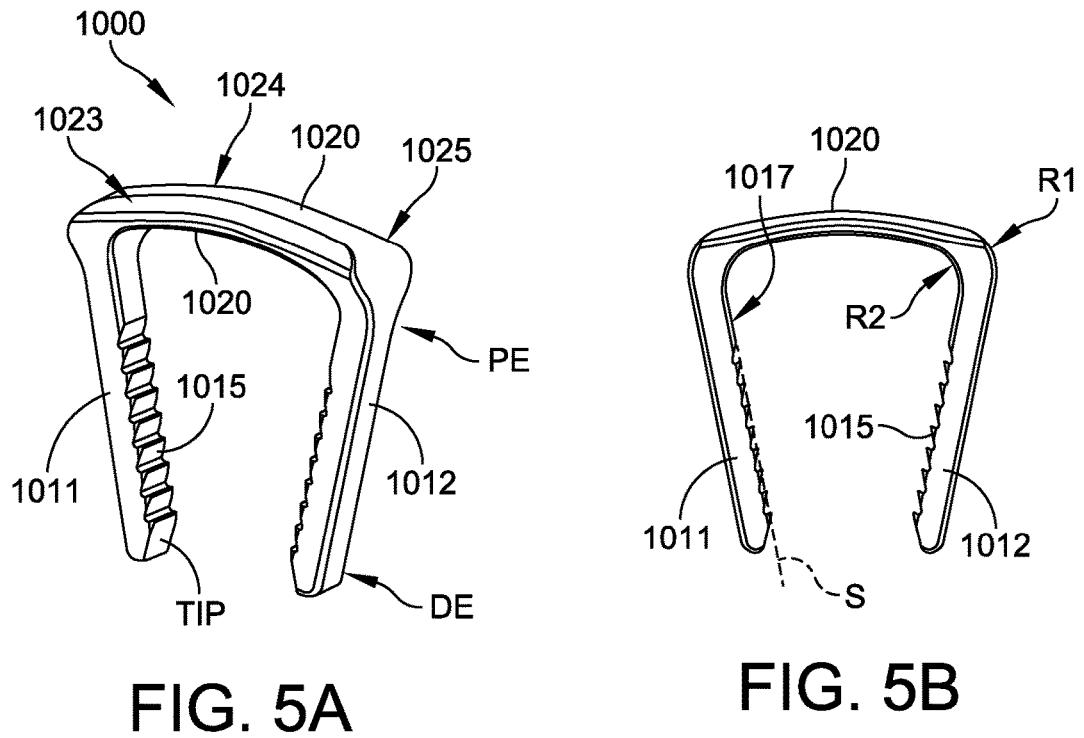
FIG. 5A
FIG. 5B
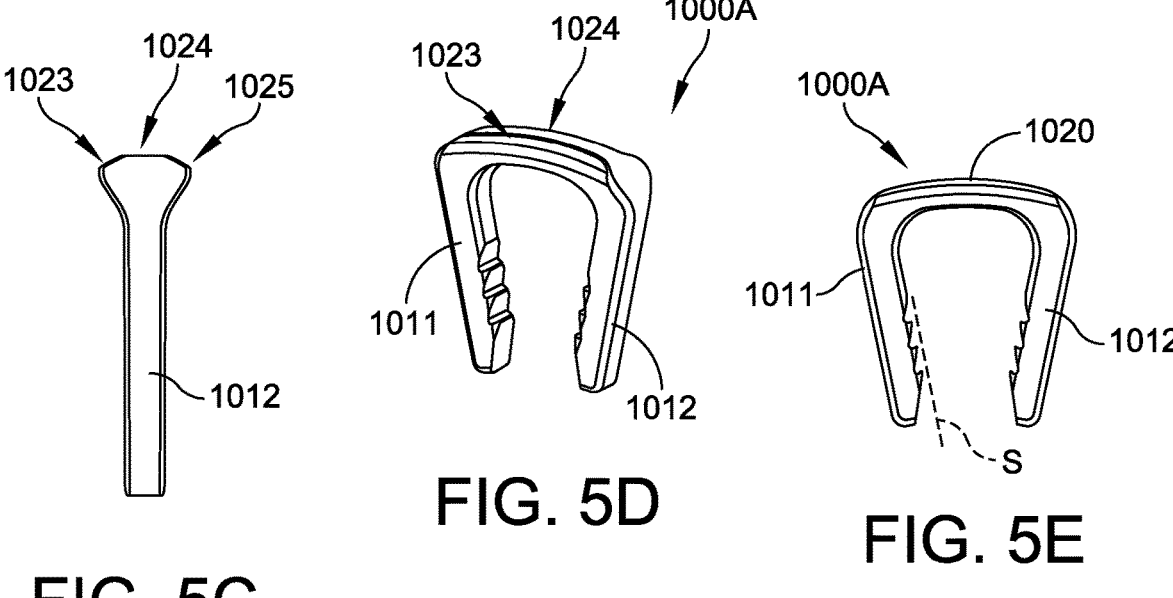
FIG. 5C
FIG. 5D
FIG. 5E

Central Position

1000

1000D

1000C

Implant Kit

Universal Instrument Kit 100, 100A, or 300

200

500A

400

500B

10

500

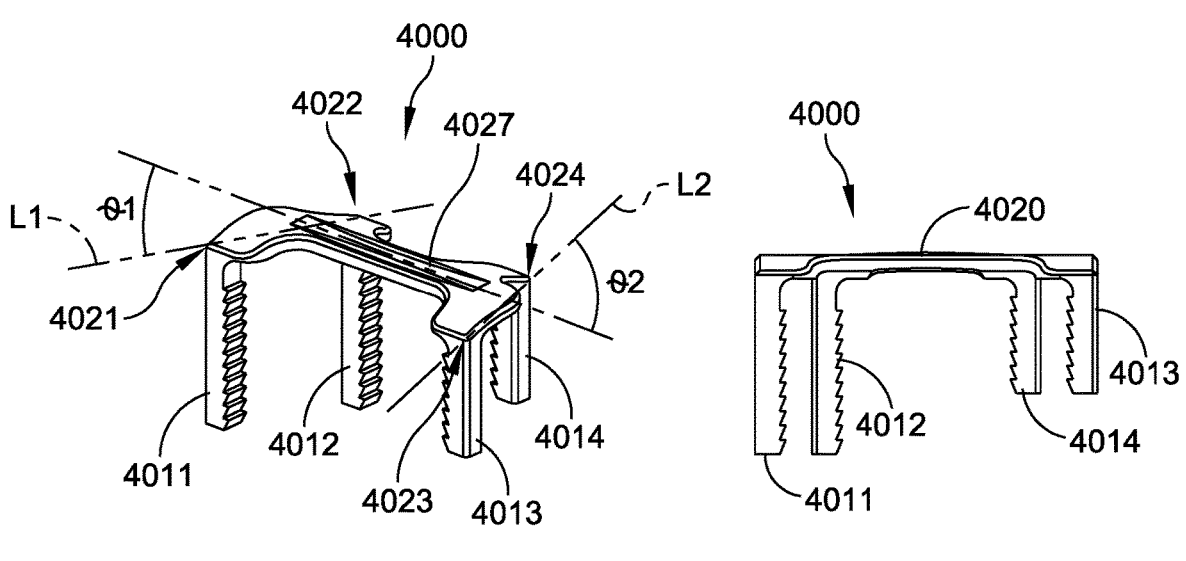
FIG. 13A                    FIG. 13B
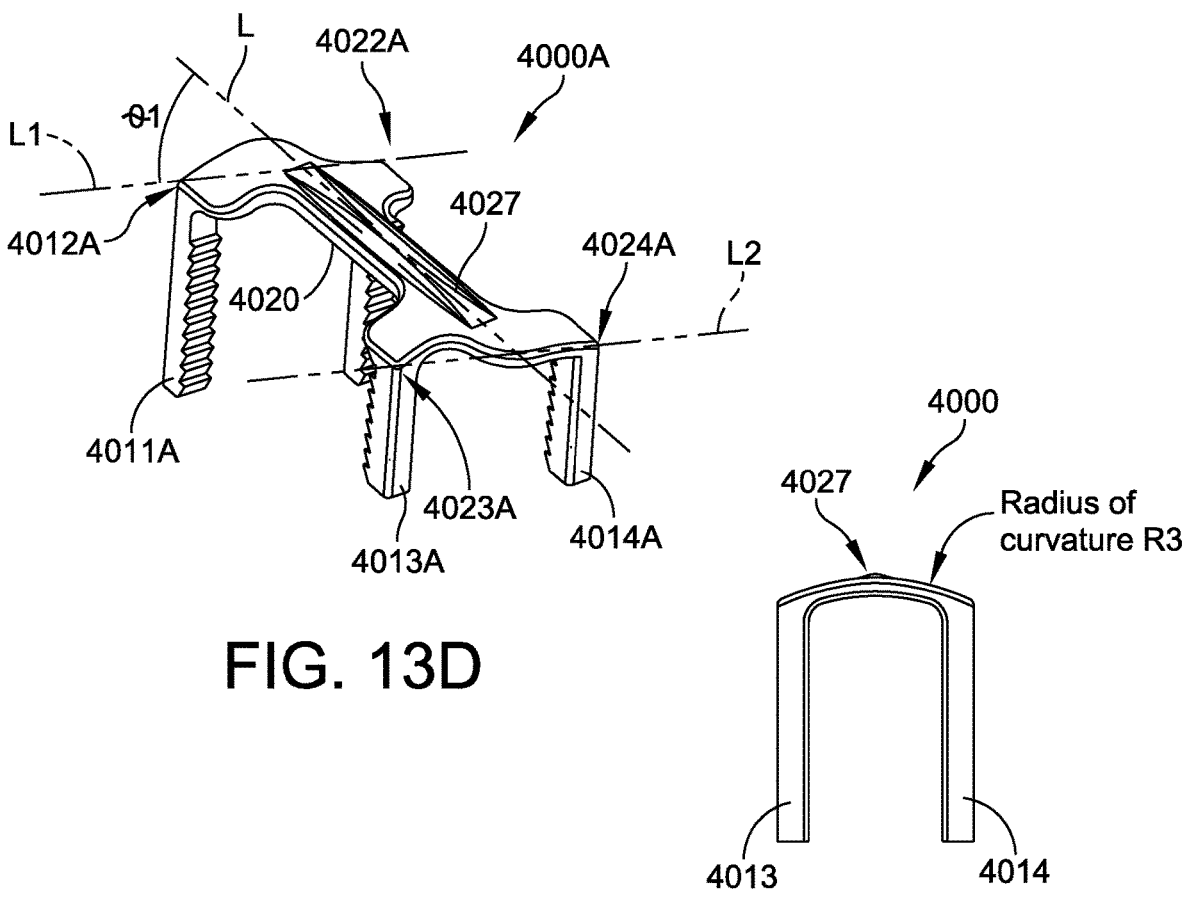
FIG. 13D
FIG. 13C (Cartridge Receiving Position)

(Staple Inserting Position)

SECTION A-A

ORTHOPEDIC STAPLE AND RELATED INSTRUMENTS

CROSS-REFERENCE TO RELATED APPLICATION

This application claims priority to U.S. application Ser. No. 17/840,673, filed on Jun. 15, 2022, the entire contents of which are incorporated herein by reference.

FIELD OF DISCLOSURE

The present disclosure relates generally to orthopedic staples.

BACKGROUND

Orthopedic staples are utilized for moving and/or maintaining bones or bone parts substantially adjacent to one another after certain surgical procedures. Moreover, orthopedic staples are often utilized to compress and hold together in place two displaced pieces of bone while healing. Often a hole or holes are necessary in the bone material for proper insertion of the surgical staples.

SUMMARY

Disclosed herein are novel orthopedic staples, related instruments, associated methods for implanting the staples at a bone repair site, and methods for removing the staples from the bone repair site.

Provided is an orthopedic drill guide assembly comprising: an elongated body having a distal end, a proximal end, and a longitudinal vertical plane defined therethrough, wherein the elongated body comprising: an outer housing having a proximal end and a distal end; and a connecting piece provided within the outer housing; a first arm and a second arm retractably connected to the distal end of the outer housing, wherein each of the first arm and the second arm comprises a distal end and a proximal end; a first drill guide sleeve located at the distal end of the first arm; and a second drill guide sleeve located at the distal end of the second arm; wherein the first drill guide sleeve and the second drill guide sleeve are separated by a spacing, wherein the proximal ends of the arms are retractably connected to the distal end of the outer housing and configured to move in a retractable motion that changes the spacing between the first drill guide sleeve and the second drill guide sleeve, wherein the proximal end of the outer housing is configured for controlling the retractable motion of the first and second arms.

Also provided is an orthopedic drill guide assembly comprising: an elongated body having a distal end and a proximal end, and a longitudinal vertical plane defined therethrough; a first guide hole and a second guide hole located near the distal end of the elongated body, wherein the first and second guide holes are arranged in a linear alignment with the longitudinal vertical plane of the elongated body such that the first guide hole is between the second guide hole and the proximal end of the elongated body; a distal sliding portion slidably engaging the distal end of the elongated body and is configured to slide back and forth along a direction that is in-line with the longitudinal vertical plane of the elongated body, wherein the distal sliding portion is communicatingly connected to the proximal end of the elongated body and the distal sliding portion's sliding motion is actuated and controlled from the proximal end of the elongated body; and a third guide hole located on the distal sliding portion and in-line with the first and second guide holes along the longitudinal vertical plane of the elongated body, wherein the first and second guide holes are located between the third guide hole and the proximal end, whereby the distal sliding portion's sliding motion changes the distance between the third guide hole and the first guide hole.

Also provided is an orthopedic drill guide assembly comprising: an elongated body having a distal end and a proximal end, and a longitudinal vertical plane defined therethrough; a first drill guide hole and a second drill guide hole located near the distal end of the elongated body, wherein the first and second drill guide holes are arranged in a linear alignment with the longitudinal vertical plane of the elongated body such that the first drill guide hole is between the second drill guide hole and the proximal end of the elongated body Also provided is a bone staple comprising: a first leg; a second leg; and a bridge connecting the two legs, the bridge comprising a top surface along the length of the bridge, wherein the top surface comprises: two chamfered edge surfaces that extend substantially the length of the bridge; and one flat surface between the two chamfered edge surfaces, wherein the flat surface extends substantially length of the bridge, wherein each of the first end and the second end of the bridge transitions down to a leg.

Also provided is a bone staple comprising: a pair of legs, each having a proximal end and a distal end, the pair of legs defining a compression plane; and a non-linearly extending bridge portion connecting the distal ends of the pair of legs, wherein the bridge portion has a generally U-shape and comprises: a flat portion that spans the distance between the distal ends of the pair of legs; and two ends of the U-shape connecting the flat portion to the proximal ends of the legs, wherein the two ends of the U-shape extending laterally between the flat portion and the proximal ends of the legs, whereby the flat portion is off-set from the compression plane; wherein the flat portion has a width that is greater than its thickness.

Also provided is a surgical staple comprising: a bridge that has an open loop configuration and a thickness from 0.05 up to 0.1 inches; two or more pairs of legs extending from the bridge in the same direction, wherein each of the legs has a surface that faces the other leg in its pair, wherein the surface comprises a plurality of barbs.

Also provided is a surgical staple comprising: a bridge having an elongated shape with a longitudinal axis defined through its length, the bridge further comprising first, second, third, and fourth corners; a first leg extending from the first corner; a second leg extending from the second corner; a third leg extending from the third corner; a fourth leg extending from the fourth corner; the bridge comprising a first section that includes the first and second corners and a second section that includes the third and fourth corners; and wherein the first and second corners are arranged such that a line connecting the first and second corners intersect the longitudinal axis of the bridge at a first non-orthogonal angle.

Also provided is a bone staple inserter kit comprising: a first sterile package containing a first bone staple securely mounted to a first cartridge, wherein the first bone staple comprises a first leg and a second leg oriented toward each other in a relaxed state, and a curved bridge portion connecting the first and second legs, wherein the first cartridge comprises a first end and a second end, the first end provided with a channel that is sized to receive the bridge portion of the first bone staple and securely hold the first bone staple by an interference fit; and a second sterile package containing; a bone staple insertion tool that is configured to receive a cartridge, like the first cartridge that has a bone staple, like the first bone staple, securely mounted thereon; a universal drill guide assembly; and a drill bit, wherein the bone staple insertion tool comprises an actuation mechanism that can transform the bone staple to an insertion shape after the cartridge with the bone staple mounted thereon is mounted on the insertion tool.

Also provided is a method to remove an orthopedic staple that is implanted in a bone repair site in its relaxed state, wherein the orthopedic staple comprises a first leg and a second leg connected by a curved bridge portion having two ends, wherein each of the two ends of the bridge portion transition down to the first leg and the second leg, respectively, the method comprising: (a) attaching an inserter tool/cartridge assembly to the orthopedic staple's bridge portion; (b) actuating the inserter tool to change the orthopedic staple from its relaxed state to its insertion state in which the two legs of the orthopedic staple are substantially parallel to each other; and (c) removing the orthopedic staple from the bone repair site.

Also provided is a method to remove an orthopedic staple that is implanted in a bone repair site in its relaxed state, wherein the orthopedic staple comprises a first leg and a second leg connected by a curved bridge portion having two ends, wherein each of the two ends of the bridge portion transition down to the first leg and the second leg, respectively, the method comprising: (a) attaching a cartridge to the orthopedic staple's bridge portion, wherein the cartridge comprises a channel that is sized to receive the curved bridge portion of the orthopedic staple and hold the orthopedic staple by an interference fit, and attaching the cartridge to the orthopedic staple's bridge portion includes engaging the channel to the curved bridge portion so that the curved bridge portion is positioned within the channel; (b) attaching an inserter tool to the cartridge; (c) actuating the inserter tool to change the orthopedic staple from its relaxed state to its insertion state in which the two legs of the orthopedic staple are substantially parallel to each other; and (d) removing the orthopedic staple from the bone repair site.

BRIEF DESCRIPTION OF THE DRAWINGS

The various embodiments of the inventive hydrogel implant of the present disclosure will be described in more detail in conjunction with the following drawing figures. The structures in the drawing figures are illustrated schematically and are not intended to show actual dimensions.

FIGS. 1A-2D illustrate an embodiment of an orthopedic drill guide assembly for predrilling holes in two bone pieces for orthopedic staples.

FIGS. 5A-5F are illustrations of shape memory metal staples having a chamfered bridge according to an embodiment.

FIGS. 13A-13D are illustrations showing another shape memory metal staple according to another embodiment.

DETAILED DESCRIPTION

Figures 1A, 1B:
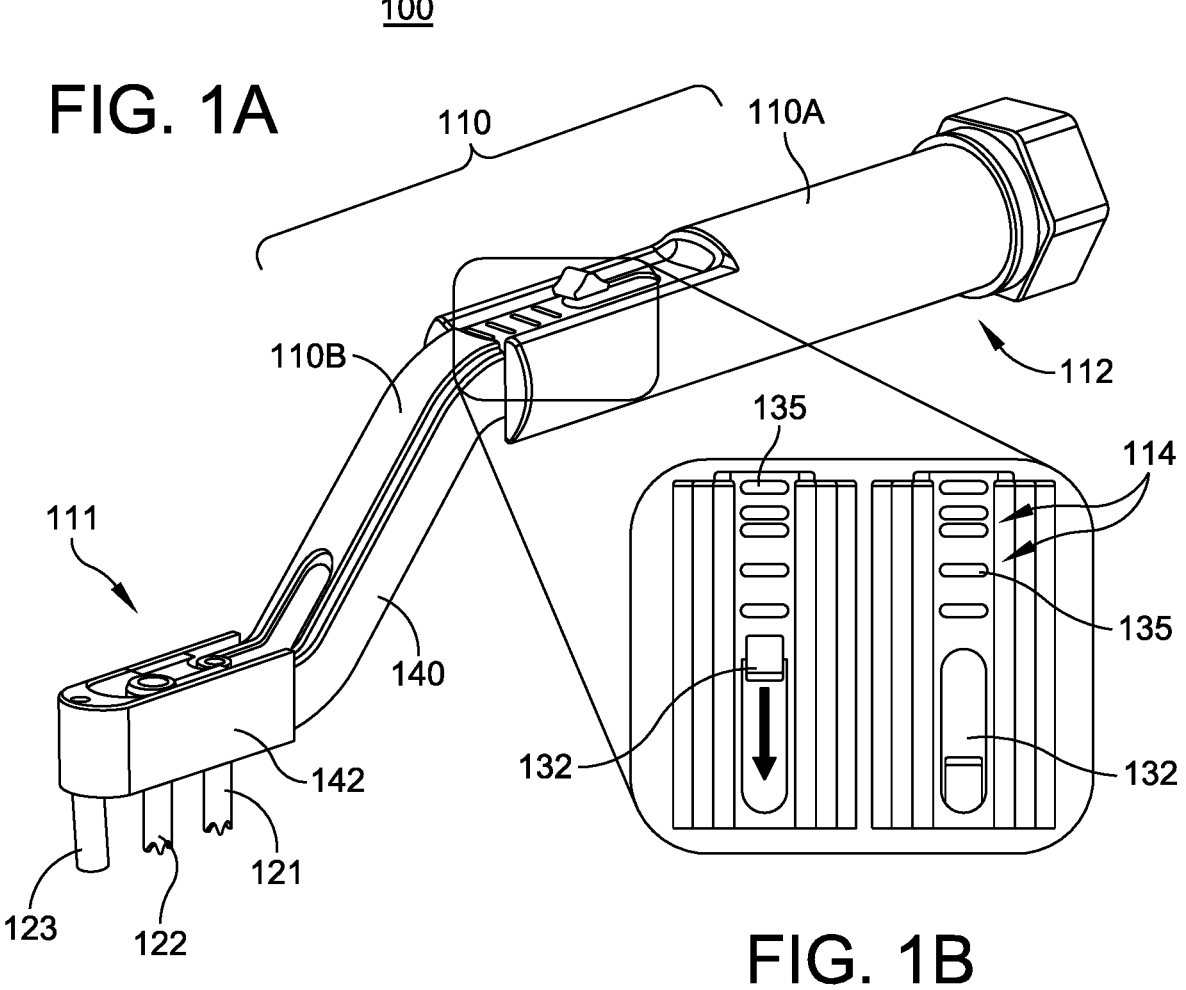

This description of the exemplary embodiments is intended to be read in connection with the accompanying drawings, which are to be considered part of the entire written description. The drawing figures are not necessarily to scale and certain features may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. When only a single machine is illustrated, the term "machine" shall also be taken to include any collection of machines that individually or jointly execute a set (or multiple sets) of instructions to perform any one or more of the methodologies discussed herein. The term "operatively connected" is such an attachment, coupling or connection that allows the pertinent structures to operate as intended by virtue of that relationship. In the claims, means-plus-function clauses, if used, are intended to cover the structures described, suggested, or rendered obvious by the written description or drawings for performing the recited function, including not only structural equivalents but also equivalent structures.

Referring to FIGS. 1A-2, an embodiment of an orthopedic drill guide assembly 100 for predrilling holes in two bone pieces for orthopedic staples is disclosed. The orthopedic drill guide assembly 100 comprises an elongated body formed by a first housing 110 having a distal end 111 and a proximal end 112, and a longitudinal vertical plane Pv defined therethrough. The first housing 110 comprises a handle portion 110A and a neck portion 110B. A first guide hole 121 and a second guide hole 122 are located near the distal end 111 of the elongated body. The first and second guide holes 121, 122, respectively, are arranged in a linear alignment with the longitudinal vertical plane Pv of the elongated body such that the first guide hole 121 is between the second guide hole 122 and the proximal end 112 of the elongated body.

The first and second guide holes 121, 122 are the drill guides that are used to predrill holes into bone repair site where an orthopedic staple will be placed. Therefore, the distance between the first and second guide holes 121, 122 is set to represent the base distance between the two legs of an orthopedic staple. The term "base distance" refers to the distance between the two legs of an orthopedic staple that is in its insertion configuration. In other words, the state where the two legs of the staple are parallel to each other and ready to be inserted into a bone repair site.

At the distal end 111 is provided a distal sliding portion 142 that slidingly engages the distal end of the elongated body and is configured to slide back and forth along a direction that is in-line with the longitudinal vertical plane of the elongated body. The distal sliding portion 142 is communicatingly connected to the proximal end 112 of the elongated body and the distal sliding portion's sliding motion is actuated and controlled from the proximal end 112 of the drill guide assembly 100. The elongated body also comprises a third guide hole 123 located on the distal sliding portion 142 and in-line with the first 121 and second 122 guide holes along the longitudinal vertical plane Pv of the elongated body. The first and second guide holes 121, 122 are located between the third guide hole 123 and the proximal end 112, whereby the distal sliding portion's sliding motion changes the distance between the third guide hole 123 and the first guide hole 121. The distal sliding portion 142 is part of a second housing 140 that connects the distal sliding portion 142, and in turn the third guide hole 123, to the proximal end 112 of the drill guide assembly 100.

The orthopedic drill guide assembly 100 further comprises a knob 160 provided at the proximal end 112 of the elongated body. The knob 160 is communicatingly connected to the distal sliding portion 142 by the second housing 140 whereby the sliding motion of the distal sliding portion 142 for changing the distance between the third guide hole 123 and the first guide hole 121 is actuated and controlled by turning the knob 160. By turning the knob 160 in one direction, the second housing 140 along with its sliding portion 142 can be made to slide toward the proximal end 112 decreasing the distance between the first and third guide holes 121, 123. By turning the knob 160 in the opposite direction, the second housing 140 and the distal sliding portion 142 can be made to slide away from the proximal end 112 increasing the distance between the first and third guide holes 121, 123.

During use, the drill guide assembly 100 is positioned over a bone repair site (e.g., joint/osteotomy/fracture) so that the first and second guide holes 121, 122 span over the repair site. In this position, the first guide hole 121 will be on one side of the repair site and the second and the third guide holes 122, 123 will be on the opposite side of the repair site. Then, a K-wire or a fixation pin (P1, P2) is placed through each of the first and third guide holes 121 and 123 then driven into the respective bone pieces on the two sides of the repair site. In the illustrated example shown in FIG. 2, one of the holes for the staple is first predrilled into one of the two bone pieces using the first guide hole 121 as a drill guide. Next, a first pin P1 is inserted through the first guide hole 121 and into the predrilled hole in the first bone piece. Next, a second pin P2 is inserted through the third guide hole 123 and into the second bone piece. Then, the knob 160 is turned to reduce the distance between the first and third guide holes 121, 123 thereby compressing the repair site (joint/osteotomy/fracture) until the two bone pieces involved are in contact. After the desired compression is achieved, the repair site should be positioned between the first and the second guide holes 121 and 122, so that the first guide hole 121 affixed to a first bone piece by the first pin P1 and the second guide hole 122 is positioned over a second bone piece. Then, the second guide hole 122 is used as a drill guide and a hole is drilled into the second bone piece. Next, the second pin P2 is removed and the drill guide 100 is removed. The surgeon can now manually compress the repair site and implant a staple into the predrilled holes. The use of the drill guide assembly 100 can be useful for predrilling holes for staples when the joint, osteotomy, or fracture have some gap between the two bone pieces. In those situations, if a shape memory metal staple is inserted without proper temporary fixation or compression of the two bone pieces, the staple will first bring the two bone pieces together and close the gap as the staple returns to its memorized shape. However, that also brings the legs of the staple inward reducing the amount of compression force the staple exerts on the repair site.

In some embodiments of the orthopedic drill guide assembly 100, rather than the knob 160, a lever can be provided at the proximal end 112 of the elongated body for actuating to pull in the third guide hole 123 toward the first guide hole 121 and reduce the distance between the third guide hole 123 and the first guide hole 121. The lever would be communicatingly connected to the distal sliding portion 142 by a connecting piece that sits within the elongated body 110, whereby the sliding motion of the distal sliding portion 142 is actuated and controlled by moving the lever.

Figure 2A:
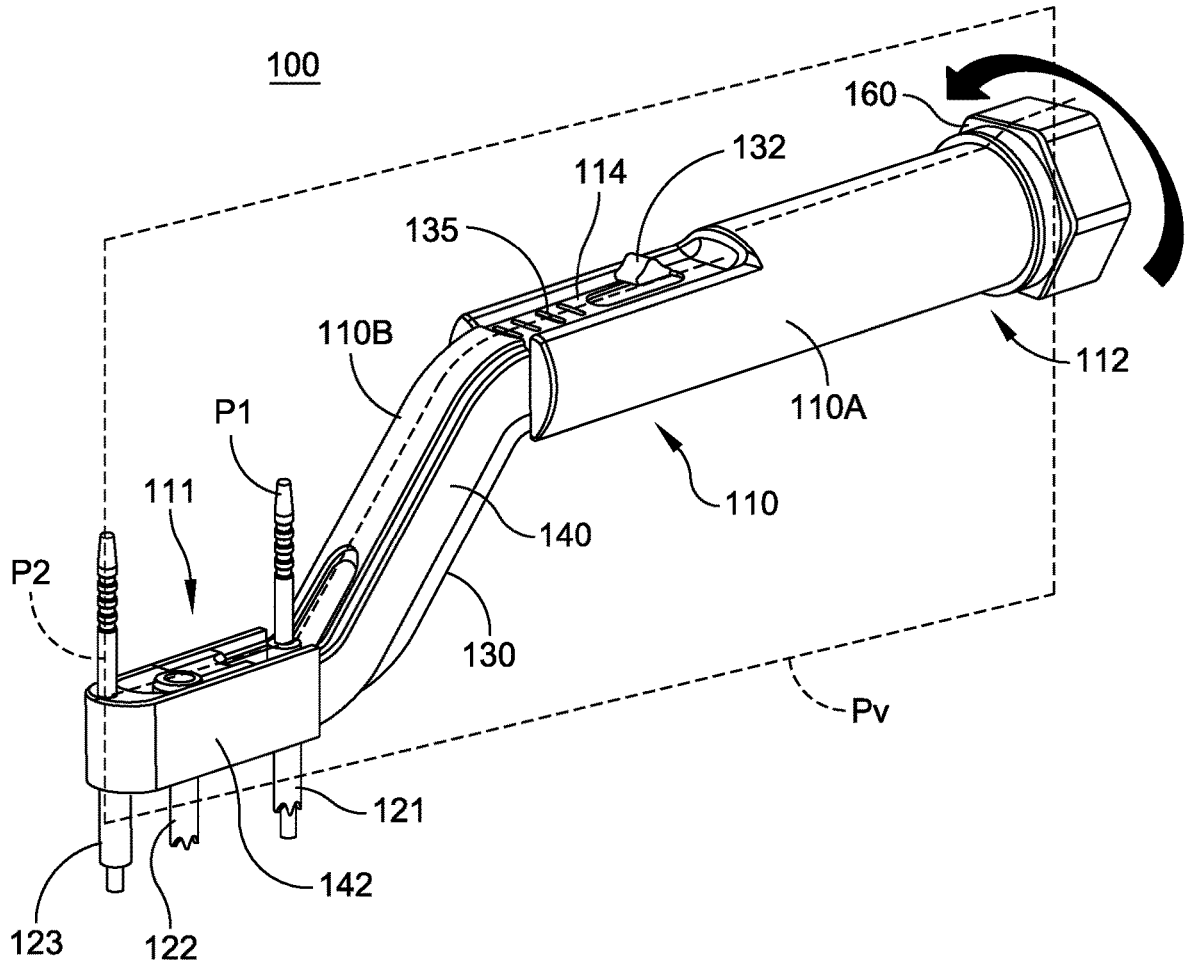
Figure 2B:
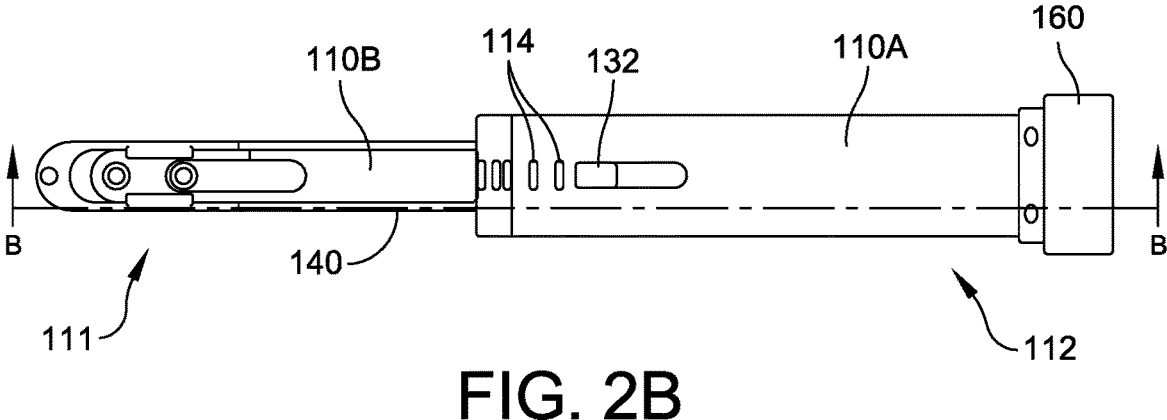
Figure 2C:
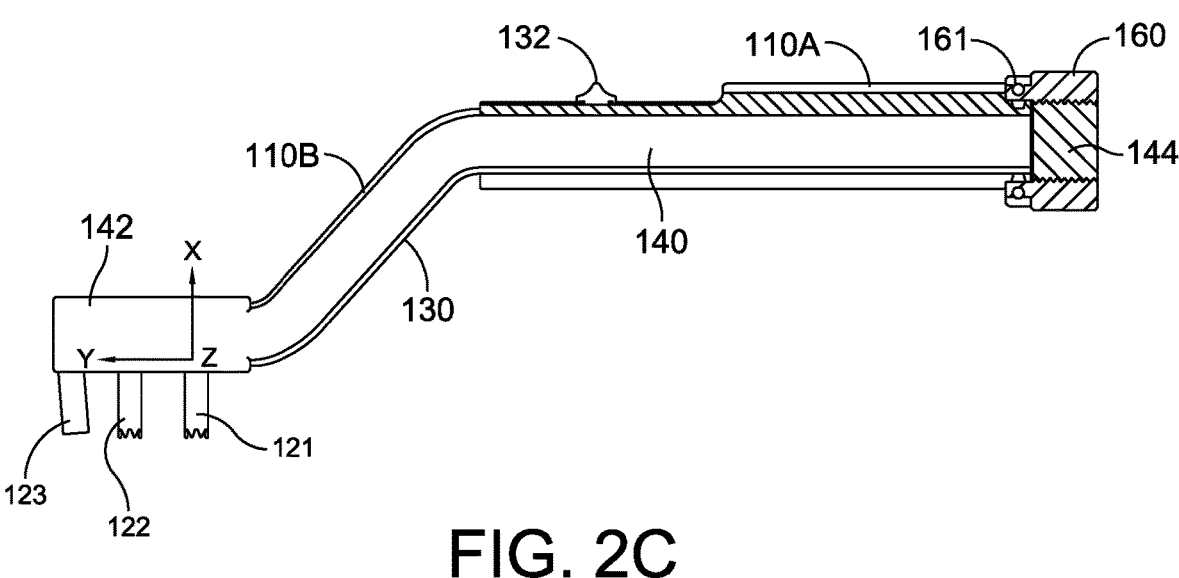
Figure 2D:
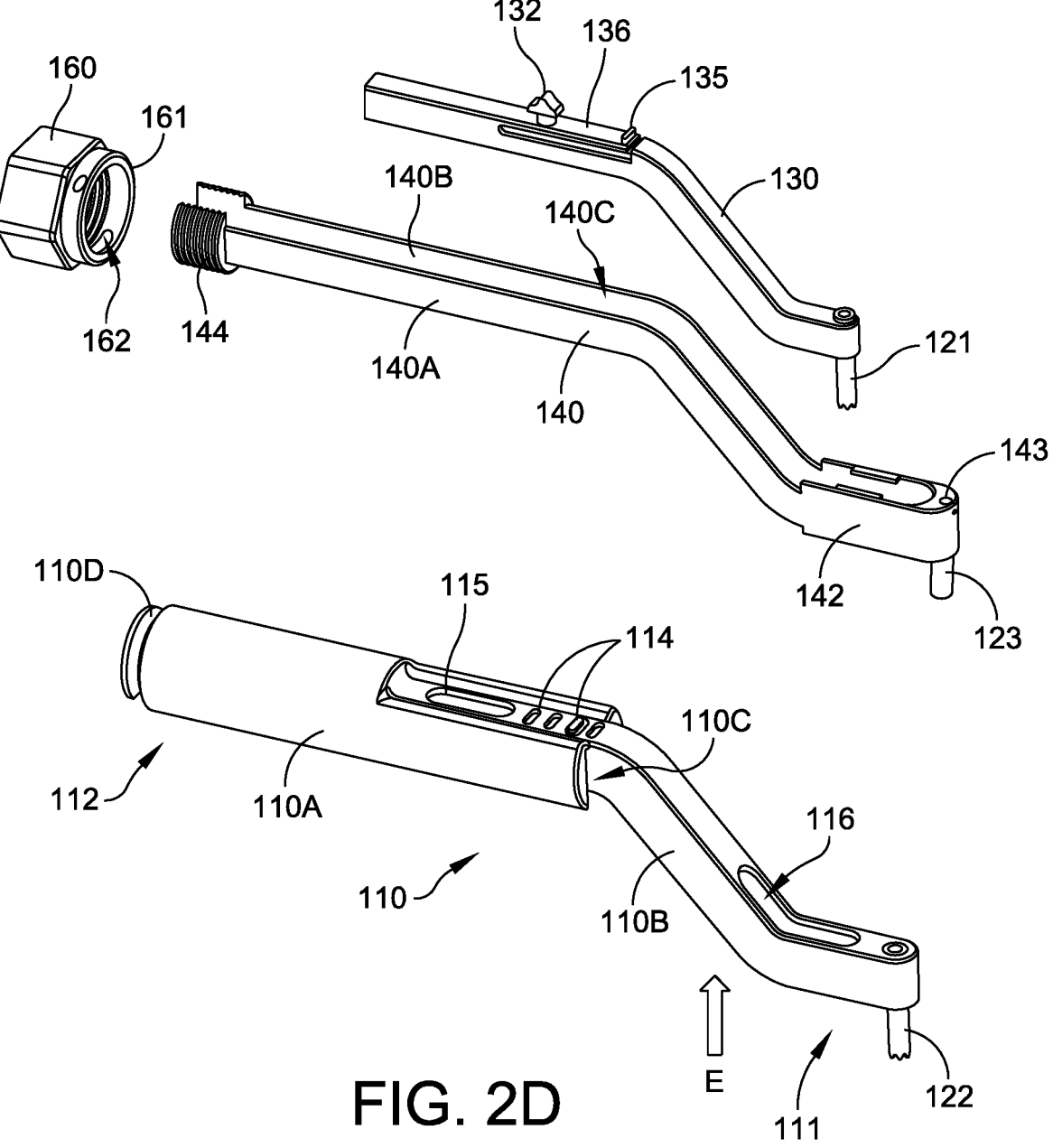

In some embodiments, the drill guide assembly 100 is configured so that the distance between the first and second guide holes 121, 122 is adjustable so that the drill guide assembly 100 can be universally used for various different staple sizes. FIGS. 2B-D illustrate in more detail an example of the internal structure of the drill guide assembly 100 that enables the feature of adjusting the distance between the first and second guide holes 121, 122. FIG. 2B is a top view of the drill guide assembly 100. FIG. 2C shows a longitudinal cross-sectional view of the drill guide assembly 100 taken through the section line B-B shown in FIG. 2B.

As shown in FIG. 2D, which is an exploded view of the drill guide assembly 100, the elongated body portion comprises three primary components: the first housing 110; the second housing 140, and a core stem 130. The second guide hole 122 is provided near the distal end 111 of the neck portion 110B of the first housing 110.

The second housing 140 comprises the distal sliding portion 142 near the distal end 111 as discussed above. The second housing 140 is formed of two elongated portions 140A, 140B. The two elongated portions are connected at the distal sliding portion 142 but are spaced apart and form a space 140C therebetween. At the proximal end 112, the two elongated portions 140A, 140B are provided with a threaded portion 144 for threadedly engaging the knob 160.

In the fully assembled drill guide assembly 100, the neck portion 110B of the first housing 110 is received in the space 140C between the two elongated portions 140A, 140B. Thus, near the distal end 111 of the drill guide assembly, the distal sliding portion 142 wraps around the neck portion 110B as shown in FIGS. 1A and 2A. The proximal half of the two elongated portions 140A, 140B, however, are positioned inside the handle portion 110A of the first housing 110. To accomplish this arrangement, the handle portion 110A is only connected to the top surface portion of the neck portion 110B and forms a spacing 110C between the handle portion 110A and the neck portion 110B as noted in FIG. 2D. The spacing 110C is open at the bottom side so that the two elongated portions 140A, 140B can slip into the spacing 110C from the bottom side. In this arrangement, the knob 160 rotatably engages the groove 110D provided at the proximal end 112 of the first housing 110 via the knob's rim 161. The threaded portion 144 of the second housing 140 is received into the interior 162 of the knob which is threaded with corresponding female threads. This arrangement can be better seen in the cross-sectional view in FIG. 2C. Thus, by turning the knob 160, the threaded engagement enables moving the second housing 140 and the distal sliding portion 142 back and forth in distal-proximal direction described above.

The neck portion 110B of the first housing 110 is open from the bottom side noted by the arrow E in FIG. 2D. In the fully assembled drill guide assembly 100, the core stem 130 is slipped into the open space within the neck portion 110B. The neck portion 110B is provided with an opening 116 to accommodate the fixation pin P1 or a drill bit that will be inserted into the first guide hole 121. The opening 116 is elongated to accommodate the full sliding motion of the core stem 130 for adjusting the spacing between the first guide hole 121 and the second guide hole 122. The core stem 130 is provided with a slider button 132 that is positioned between the first guide hole 121 and the proximal end 112 of the drill guide assembly 100.

The core stem 130 is also provided with a visual marker tab 135. The handle portion 110A can comprise an elongated opening 115 through which the slider button 132 protrudes to allow the user to push pull on the slider button 132 to move the core stem 130 back and forth to move the first guide hole 121 back and forth along a direction (distal-proximal) that is in-line with the longitudinal vertical plane Pv of the drill guide assembly 100.

The handle portion 110A can also comprise a plurality of slots 114 through which the visual marker tab 135 can at least partially protrude for indicating the position of the first guide hole 121 with respect to the second guide hole 122. Because the first and second guide holes 121, 122 are the drill guide holes that will be used to drill holes for the bone staples, this ability to change the spacing between the first and second guide holes 121, 122 allow the drill guide assembly 100 to be used for many different sizes of staples.

Therefore, the plurality of slots 114 can be located at preset distances representing particular staple size that corresponds to the selected distance between the first and second guide holes 121, 122. Each of the plurality of slots 114 corresponds to a particular staple size and the visual marker tab 135 can be a colored marking that moves along with the slider button 132 so that the user can see the marker through the slots 114 and tell when a desired spacing between the first and second guide holes 121, 122 has been selected corresponding to the desired staple size. In some embodiments, by having the visual marker tab 135 at least partially protrude through the slots 114, the visual marker tab 135 can be made to click through the slots 114 thus providing additional tactile feedback to the user. As shown in FIG. 2D, the portion 136 of the core stem 130 on which the slider button 132 and the visual marker tab 135 reside can be configured to be a cantilevered structure to allow the slider button 132 and the visual marker tab 135 to be pressed down during the sliding motion. Additionally, when the visual marker tab 135 pops into a slot 114, the visual marker tab can prevent unintended movement of the slider button 132 and lock drill guide assembly to the selected staple size.

In the drill guide assembly 100, the second guide hole 122 is provided on the first housing 110 at a fixed location. The second guide hole 122 is referred to as being at a fixed location because it is the first guide hole 121 that moves with respect to the position of the second guide hole 122 in the frame of reference of the drill guide assembly 100. By moving the first guide hole 121, the distance between the first guide hole 121 and the second guide hole 122 can be adjusted.

The handle portion 110A is shaped to make it comfortable for the user to grab and hold the drill guide 100. The slider button 132 can be provided in the handle portion so that the user can manipulate the slider button 132 with the user's thumb for one-handed operation.

FIG. 1B illustrates two different top-down views of the slots 114, the slider button 132, and the visual marker tab 135, each view illustrating two different staple size selection. In the view shown on the left side, the slider button 132 is in its most distal position (closest to the distal end 111 of the drill guide assembly. In this example, when the slider button 132 is in this position, the first guide hole 121 is at its closest to the second guide hole 122. Thus, this position represents selection for the smallest staple size. In the view shown on the right side of FIG. 1B, the slider button 132 is in its most proximal position (closest to the proximal end 112 of the drill guide assembly. In this example, when the slider button 132 is in this position, the first guide hole 121 is at its furthest from the second guide hole 122. Thus, this position represents selection for the largest staple size.

Figures 3A, 3B:
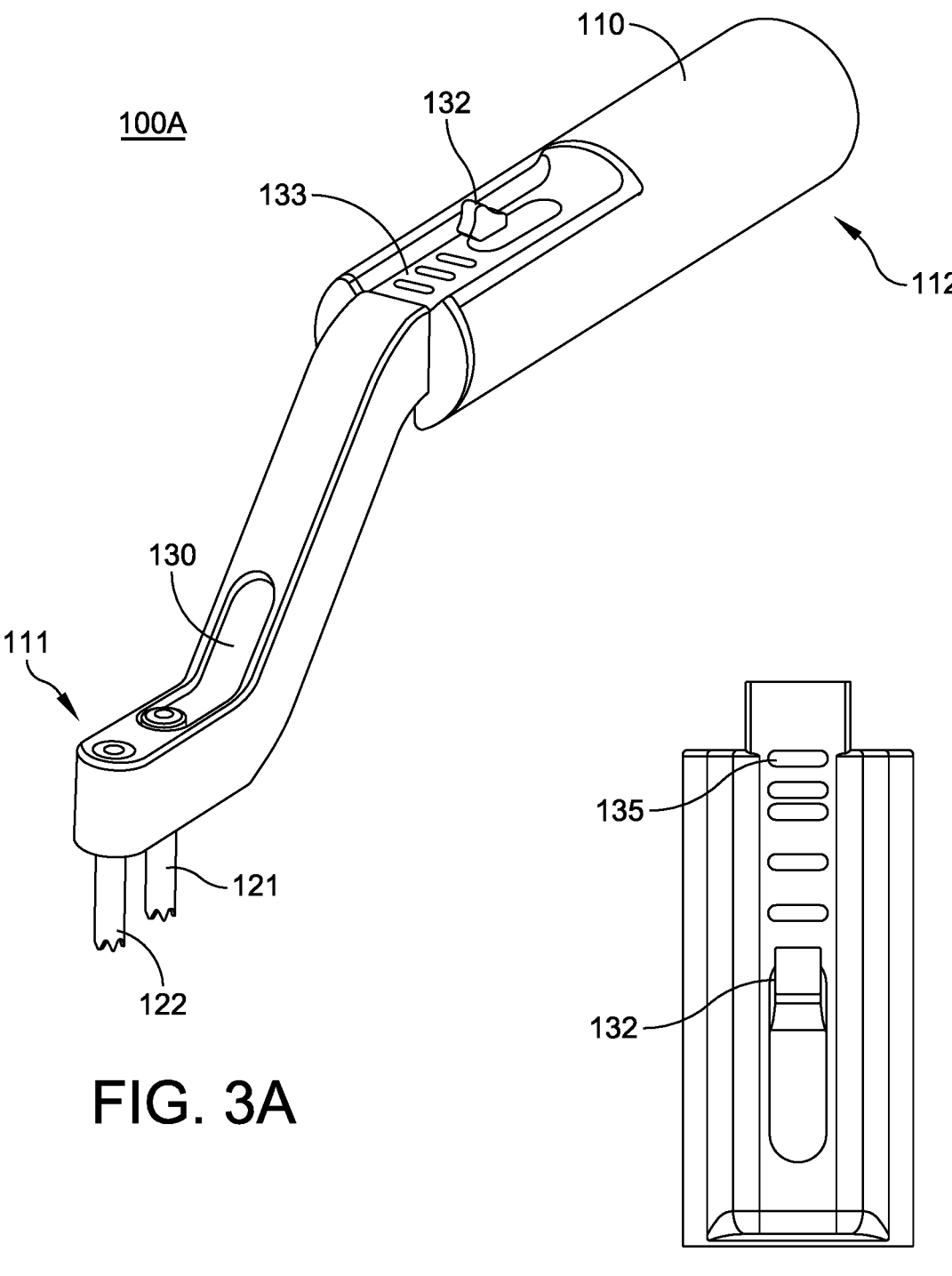
FIGS. 3A and 3B illustrate another embodiment of an orthopedic drill guide assembly for predrilling holes in two bone pieces for orthopedic staples.

Referring to FIGS. 3A-3B, according to another aspect, a simpler drill guide assembly 100A is disclosed. The drill guide assembly 200 is similar in construction as the drill guide assembly 100A but the drill guide assembly 200 is not configured to perform the pre-drilling temporary compression of the repair site. The drill guide assembly 100A does not have the third guide hole 123 of the drill guide assembly 100. The drill guide assembly 100A comprises the same first and second guide holes 121, 122, the slider button 132 and the plurality of slots 114 as in the drill guide assembly 100. Thus, drill guide assembly 100A is useful for predrilling holes in two bone pieces in a repair site for a staple.

Referring to FIGS. 4A-4H, an orthopedic drill guide assembly 300 according to another embodiment is disclosed. The drill guide assembly 300 comprises an elongated body 305 having a distal end 311 and a proximal end 312, and a longitudinal vertical plane Pv defined therethrough. The elongated body 305 comprises an outer housing 310 having a proximal end and a distal end, and a connecting piece 370 provided within the outer housing 310. The drill guide assembly 300 also comprises a first arm 351 and a second arm 352 retractably connected to the distal end 311 of the outer housing 310. The first arm 351 comprises a distal end 351A and a proximal end 351B. The second arm 352 comprises a distal end 352A and a proximal end 352B.

The distal ends 351A, 352A of the first and second arms 352, 352, respectively, are provided with a first drill guide sleeve 321 and a second drill guide sleeve 322, respectively. The first drill guide sleeve 321 and the second drill guide sleeve 322 are separated by a spacing D (See FIG. 4B).

The proximal ends 351B, 352B of the arms are retractably connected to the distal end 311 of the outer housing 310 and configured to move in a retractable motion that changes the spacing D between the first drill guide sleeve 321 and the second drill guide sleeve 322.

The drill guide assembly 300 further comprises a knob 350 provided at the proximal end 312 of the outer housing 310 for actuating and controlling the retractable motion of the first and second arms 351, 352. The knob 350 is communicatingly connected to the first and second arms 351, 352.

Figure 4A:
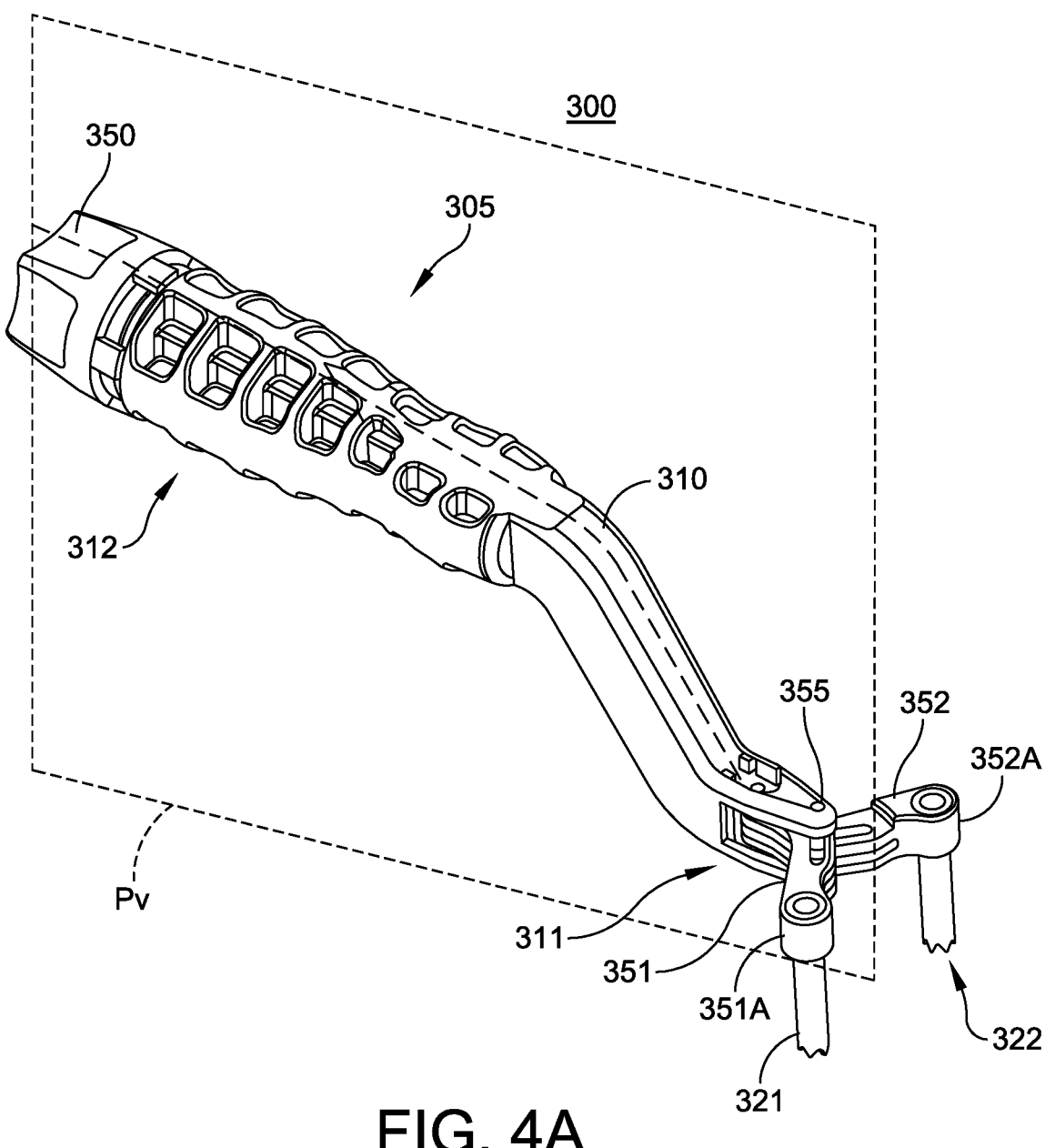
FIGS. 4A to 4H illustrate another embodiment of an orthopedic drill guide assembly for predrilling holes in two bone pieces for orthopedic staples.
Figure 4B:
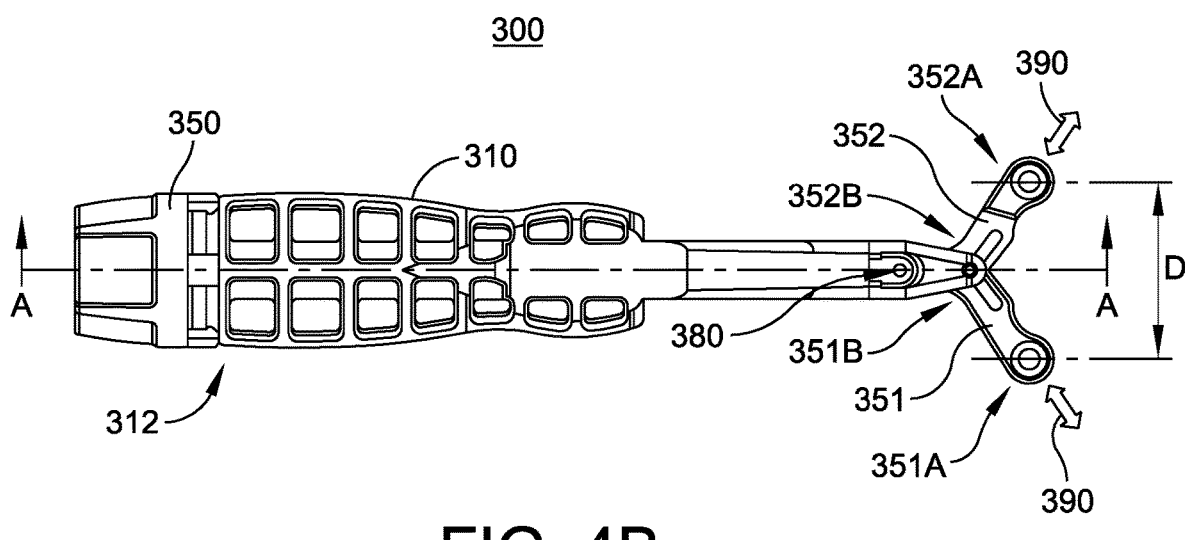
Figure 4C:
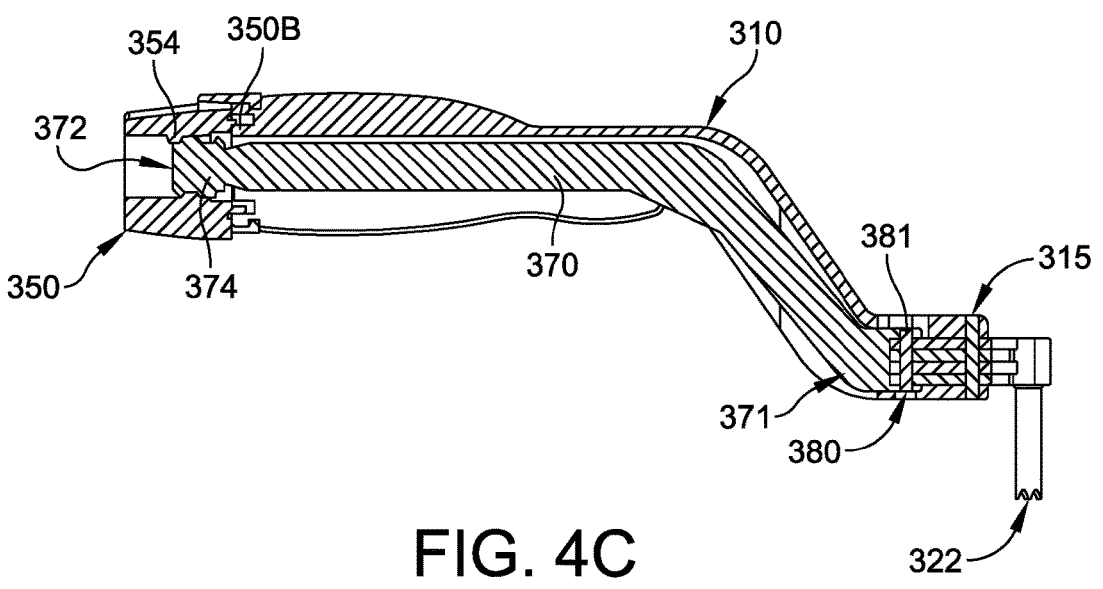

FIG. 4C shows a longitudinal cross-section of the drill guide assembly 300 where the section is taken through the line A-A shown in FIG. 4B. The connecting piece 370 has a proximal end 372 and a distal end 371 and extends through the outer housing 310 and provides the communicating connection between the knob 350 and the first and second arms 351, 352.

The knob 350 is connected to the proximal end 372 of the connecting piece 370 and the connection between the knob 350 and the connecting piece 370 is configured to move the connecting piece 370 back and forth between the distal end 311 and the proximal end 312 of the outer housing 310.

The proximal ends 351B, 352B of the first and second arms 351, 352, respectively, are pivotally connected to a pivot point 380 located at the distal end 371 of the connecting piece 370. The pivot point 380 is on the longitudinal vertical plane Pv. The pivotal connection at the pivot point 380 is made by a pivot pin 381.

Figure 4D:
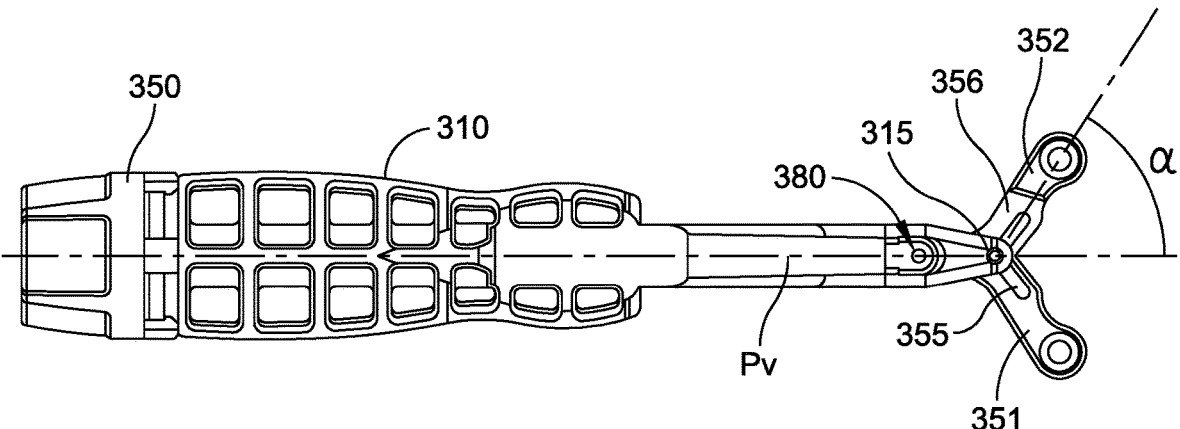
Figure 4E:
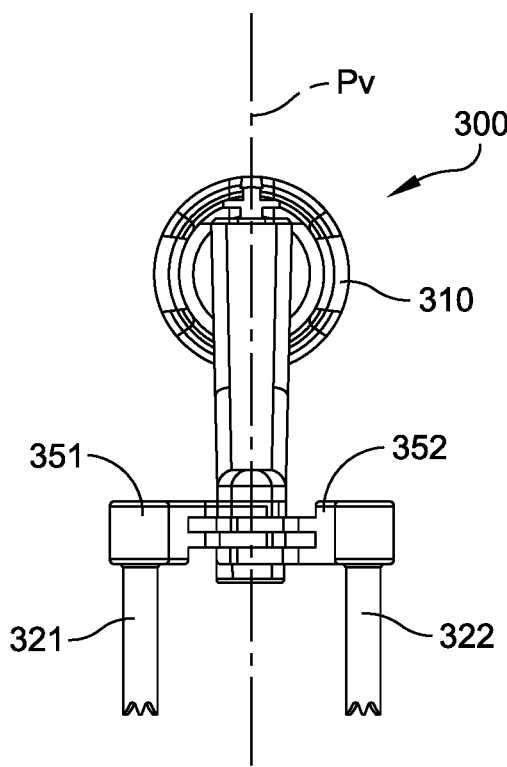
Figure 4F:
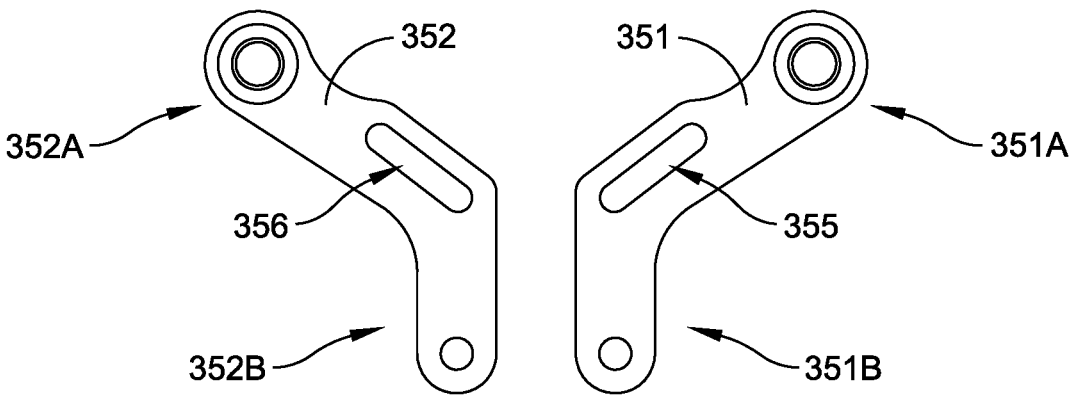
Figure 4G:
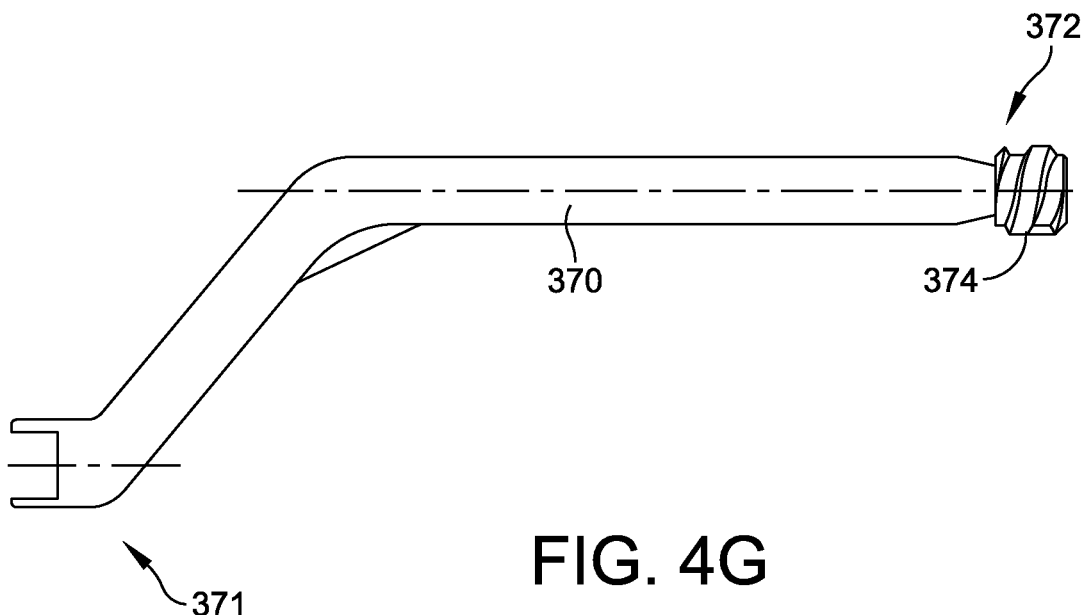

Referring to FIG. 4F, each of the first and second arms 351, 352 are configured with an elongated slot 355, 356, respectively, that extends between the arm's proximal end 351B, 352B and the distal end 351A, 352A. The first and second arms 351, 352 are arranged so that the elongated slot 355, 356 on each of the first and second arms 351, 352 is oriented outward at an acute angle α from the longitudinal vertical plane Pv of the elongated body 305. The first and second arms 351, 352 overlap one another at their proximal ends 351B, 352B where the pivotal connection is made and a portion of the elongated slots 355, 356 overlap one another. The distal end 311 of the outer housing 310 comprises a fixed pin 315 that extends through both of the elongated slots 355, 356 at the overlapping portion, wherein the fixed pin 315 is on the longitudinal vertical plane Pv. As noted above, the pivot point 380 and the fixed pin 315 are both on the longitudinal vertical plane Pv. The fixed pin 315 keeps the two arms 351, 352 from freely pivoting about the pivot point 380 without control. This arrangement allows the user to control the retractable motion of the first and second arms 351, 352 by moving the connecting piece 370 back and forth using the knob 350. The back and forth motion of the connecting piece 370 produces the retractable motion of the first and second arms 351, 352 shown by the arrows 390 in FIG. 4B. The retractable motion of the first and second arms 351, 352 changes the spacing D between the first drill guide sleeve 321 and the second drill guide sleeve 322.

FIGS. 4B and 4D are illustrations of the drill guide assembly 300 with its first and second arms 351, 352 in their fully extended configuration. The connecting piece 370 has been pushed toward the distal end 311 of the outer housing 310 as far as it can go. In turn, the connecting piece 370 has pushed the first and second arms 351, 352 to their fully extended position because the first and second arms 351, 352 are connected to the connecting piece 370 by the pivot pin 381. As can be seen, each arm has been pushed out to its maximum extension and the fixed pin 315 is at the most proximal ends of the two slots 355, 356. In this configuration, the spacing D between the first and second arms is at its maximum.

Figure 4H:
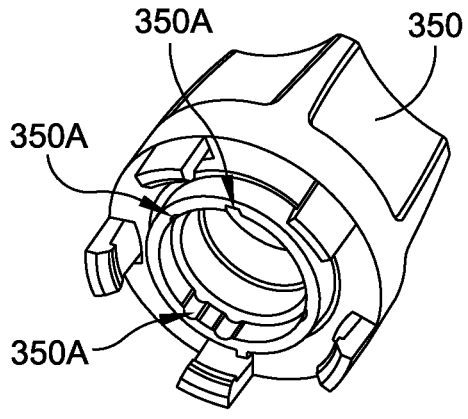

In some embodiments of the drill guide 300, the knob 350 and the connecting piece 370 are connected by screw thread arrangement that enables the back and forth movement of the connecting piece 370 by turning the knob 350. In the illustrated example shown in FIGS. 4C and 4G, the proximal end 372 of the connecting piece 370 is configured with a male screw thread 374. As shown in FIGS. 4C and 4H, the internal bore of the knob 350 is provided with a female screw thread 354 that threadedly engage the proximal end 372 of the connecting piece 370.

In some embodiments of the drill guide 300, the knob 350 can be configured to have a clicking feature as the knob is rotated. Such clicking feature provides both tactile and aural feed back to the user so that the user knows where each position is when the knob is turned to the preset locations correlating to the sizes of the staples. The knob 350 can be provide with grooves 350A as shown in FIG. 4H that interact with a protrusion 350B (See FIG. 4C) on the proximal portion of the outer housing 310.

In some embodiments of the drill guide 300, each of the first and second drill guide sleeves 321, 322 are provided with a hole sized to receive a drill bit. As shown in FIGS. 4A and 4E, in some embodiments of the drill guide, each of the first and second drill guide sleeves 321, 322 extend parallel to each other.

Preferably, the connecting piece 370 moves back and forth along the longitudinal vertical plane Pv.

Referring to FIGS. 5A-5E, according to another aspect of the present disclosure, a surgical bone staple 1000 having a chamfered bridge portion is disclosed. The surgical bone staple 1000 comprises a first leg 1011, a second leg 1012, and a bridge 1020 connecting the two legs. The bridge 1020 has a top surface 1022 along the length of the bridge between a first end and a second end. The top surface 1022 comprises two chamfered edge surfaces 1023 and 1025 that extend substantially the length of the bridge 1020 and one flat surface 1024 between the two chamfered edge surfaces 1023, 1025. The flat surface 1024 also extends substantially the length of the bridge 1020. As shown in the end-view of the staple 1000 in FIG. 5C, the bridge 1020 portion is wider than the width of the first and second legs 1011, 1012. This makes the bridge 1020 stronger and more resistant to unwanted bending in the lateral plane. In this context the lateral plane refers to the plane that is substantially orthogonal to the legs.

In some embodiments, each of the two legs 1011, 1012 comprises an inner surface 1017 and a plurality of barbs or teeth 1015 configured to prevent backing out of the staple after installation in a bone. Each of the plurality of barbs 1015 are formed by removing material between each barb such that the pointed tips of the barbs do not protrude beyond the inner surface of the legs. This is shown in FIGS. 5B and 5E by the dotted line S that represents the inner surface of the legs.

Each of the two legs 1011, 1012 comprises a proximal end PE and a distal end DE and each distal end includes a wedge-shaped tip. In this context, the term "proximal" refers to the end of a staple leg that is attached to the bridge 1020 and the term "distal" refers to the end of a staple leg that is away from the bridge 1020. Each of the two ends of the bridge transitions down to a leg. The transition from the bridge 1020 to the legs along the top surface 1024 of the bridge has a first radius of curvature R1 and the transition from the bridge to the legs along the bottom surface of the bridge has a second radius of curvature R2, wherein R1>R2. Preferably, R1=0.110 inches and R2=0.100 inches. In some embodiments, the bone staple 1000 is comprised of a shape memory material such that the staple is movable between an insertion shape and a relaxed shape.

Figure 5F:
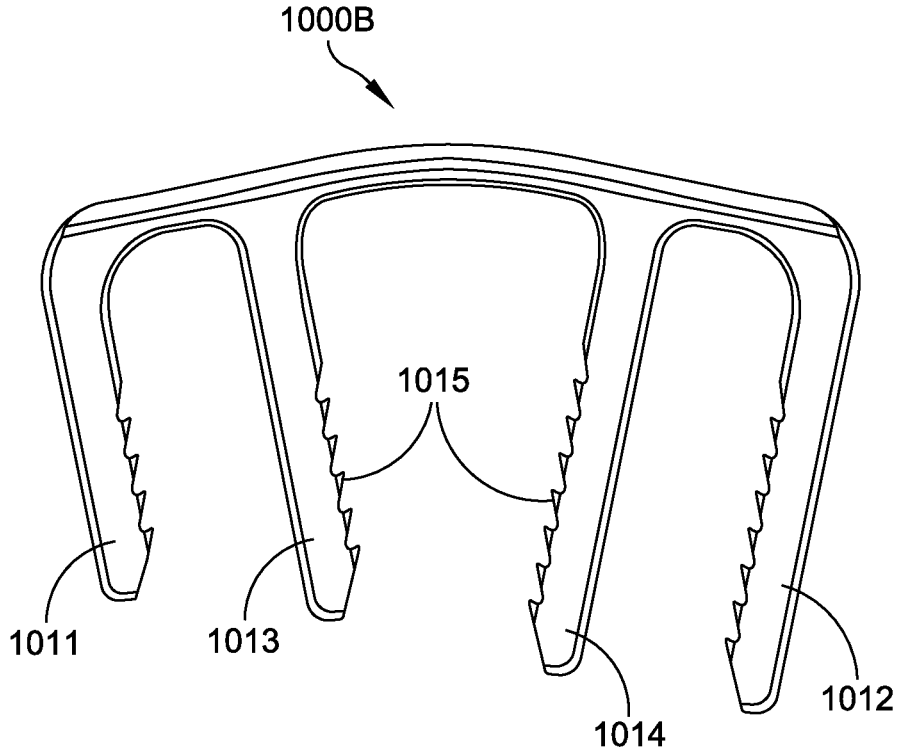

FIGS. 5D and 5E are illustrations of a bone staple 1000A that has all the features of the bone staple 1000 discussed above but is a smaller sized staple. According to another embodiment, the bone staple 1000 can have more than two legs. FIG. 5F shows a bone staple 1000B that is an example of such variation. The bone staple 1000B comprises four legs 1011, 1012, 1013, 1014. Two pairs of legs 1011, 1013 and 1012, 1014 are provided. The first pair of legs 1011, 1013 is on one side of the staple 1000B and the second pair of legs 1012, 1014 is on the other side of the staple 1000B. In some embodiments, each of the legs can have different lengths as desired.

Referring to FIGS. 10A-10D, according to another aspect, a bone staple 2000 having an offset bridge portion is disclosed. The bone staple 2000 comprises a pair of legs 2011, 2012, each having a proximal end PE and a distal end DE. The pair of legs 2011, 2012 define a compression plane CP. The bone staple 2000 also comprises a non-linearly extending (i.e., offset) bridge portion 2020 connecting the proximal ends of the pair of legs. The bridge portion 2020 has a generally U-shape and comprises a flat portion 2024 that spans the distance between the proximal ends of the pair of legs. Two ends of the U-shape connect the flat portion 2024 to the proximal ends PE of the legs 2011, 2012. The two ends of the U-shape extend laterally between the flat portion 2024 and the proximal ends PE of the legs 2011, 2012. The flat portion 2024 is offset from the compression plane CP. The flat portion 2024 has a width that is greater than its thickness to provide enhanced lateral stiffness. The ratio of the width/thickness of the flat portion 2024 can be about 2.0 to 2.5.

In some embodiments of the bone staple 2000, the legs 2011, 2012 comprise inner surfaces 2017 that are facing one another and a plurality of barbs 2015 along the inner surfaces 2017.

Figure 10A:
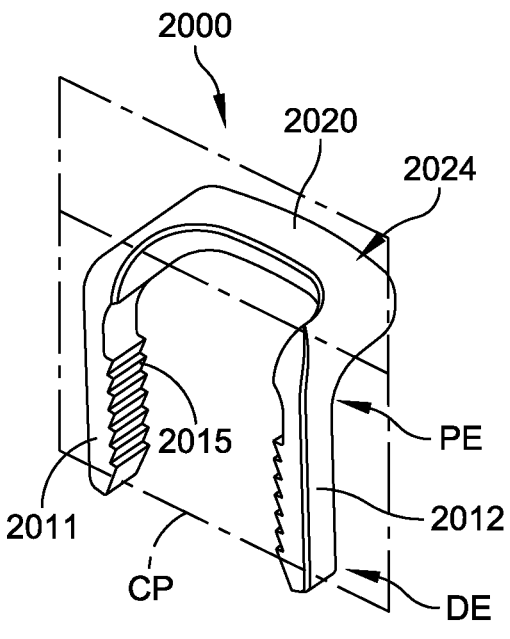
FIGS. 10A-10D are illustrations of shape memory metal staples having an offset bridge according to an embodiment.
Figure 10B:
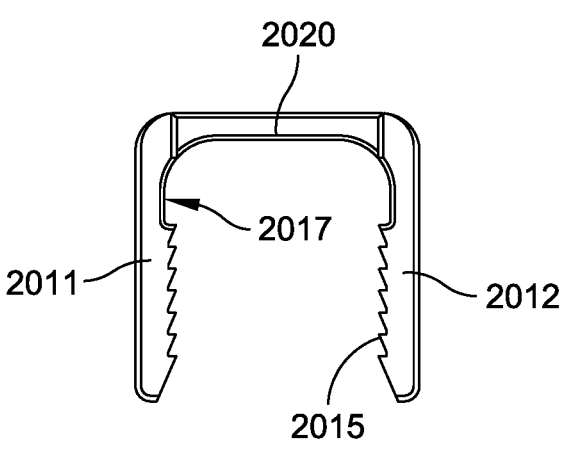
Figure 10C:
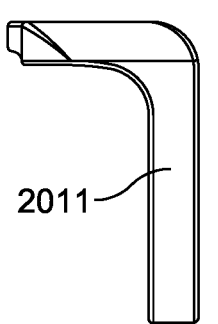
Figure 10D:
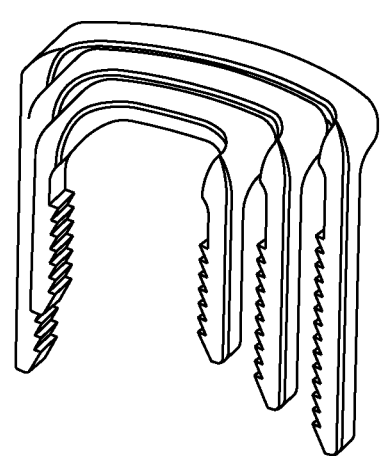

FIG. 10C is a side view of the bone staple 2000. FIG. 10D is an illustration showing an example of three different size offset bridge bone staples in a nested arrangement. This illustration of the nested arrangement shows that the bone staple embodiment 2000 of different sizes can be used to place multiple staples in close proximity to each other in the patient.

In some embodiments, the bone staple 2000 can be comprised of a shape memory material such that the staple can be movable between an insertion state where the staple 2000 assumes an insertion shape and a relaxed state where the staple 2020 assumes an implanted shape. In FIG. 10A, the offset bone staple 2000 is in its relaxed state and as such the configuration shown is its implanted shape with the two legs 2011, 2012 being in their closest positions. In the insertion shape, the open ends of the U-shaped bridge portion 2020 are spread apart outward so that the two legs 2011, 2012 are further apart. In use, the staple 2000 is inserted into a bone repair site in its insertion shape so that the two legs 2011, 2012 straddle a break in the bone. After the two legs 2011, 2012 are inserted into a bone repair site, the staple 2000 is returned to its relaxed state causing the U-shaped bridge portion 2020 to close the two legs 2011, 2012 and closing the break in the bone.

Figure 11A:
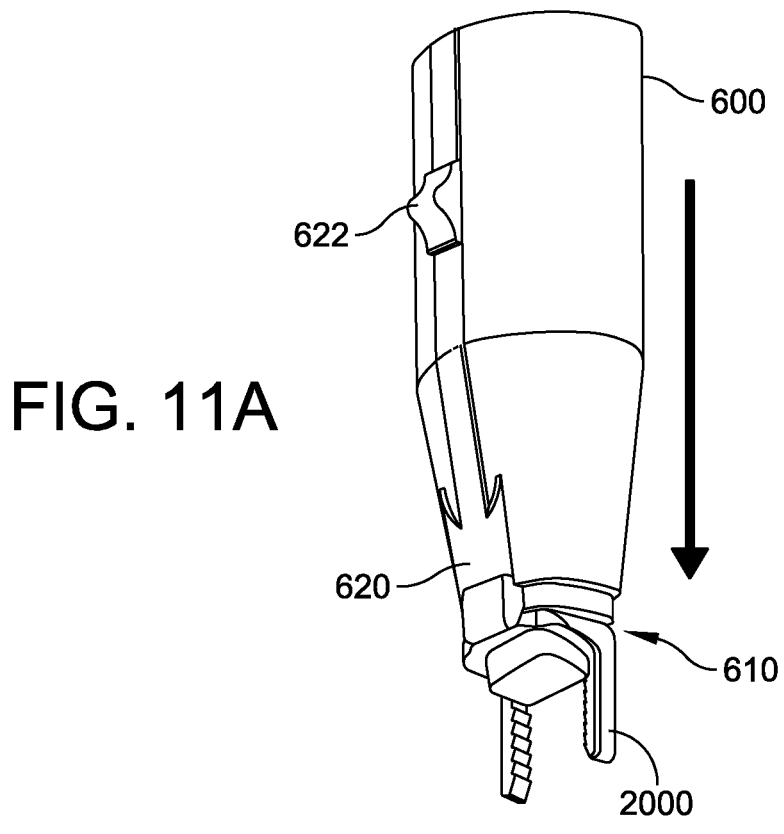
FIGS. 11A-11C are illustrations showing a staple inserter for the offset bridge staples of FIGS. 10A-10D.
Figure 11B:
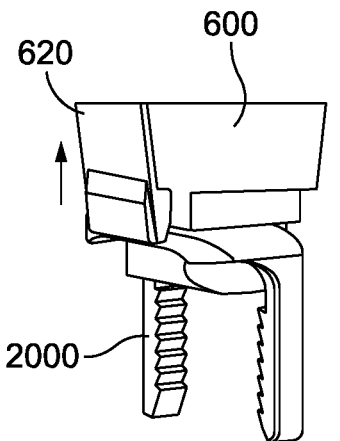
Figure 11C:
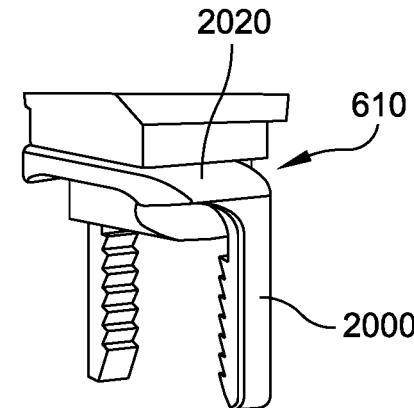

The transition of the offset staple 2000 between its insertion state and the relaxed state and vice versa is achieved using a staple inserter tool 600 shown in FIGS. 11A-11C. The staple inserter 600 comprises a working portion that is configured with a channel 610 for receiving and holding the bone staple 2000 having an offset bridge 2020. The channel 610 is sized to receive the bridge portion 2020 of the bone staple 2000 and securely hold the bone staple 2000 by an interference fit.

The inserter 600 is configured with a slider 622 that a user can use to slide a cam 620 toward or away from the bridge portion 2020 of the staple 2020 held in the channel 610. When the cam 620 is pushed toward the bridge portion 2020 and engage the bridge portion 2020, the cam 620 generates a lateral urging force against the bridge portion 2020. "Lateral" herein means orthogonal to the longitudinal axis of the inserter 600. As can be seen in FIGS. 10A and 10B, the top and bottom surfaces of the bridge portion 2020 is flat when viewed from lateral side but the U-shape of the bridge portion 2020 presents a convex portion toward the cam 620 when the staple 2020 is held in the channel 610. When the cam 620 pushes against the convex portion of the U-shaped bridge portion 2020, the lateral urging force causes the two legs 2011, 2012 at the ends of the U-shape to spread open thus deforming the offset staple 2000 into its insertion shape. Once the staple 2020 is placed in the bone repair site using the inserter 600, the slider 622 can be pulled back withdrawing the cam 620 away from the bridge portion 2020. This action removes the lateral urging force from the bridge portion 2020 and allows the bridge portion 2020 to return to its relaxed state causing the U-shaped bridge portion 2020 to close the two legs 2011, 2012 and closing the break in the bone.

Referring to FIGS. 12A-12E, a bone staple 3000 according to another embodiment is disclosed. Two or more pairs of legs 3011, 3012, 3013, 3014 extend from the bridge 3020 all in the same direction. Each of the legs 3011, 3012, 3013, 3014 has a surface that faces the other leg in its pair, where the surface comprises a plurality of barbs 3015. In the illustrated example, the bone staple 3000 is shown with two pairs of legs: 3011 and 3012 being one pair and 3013 and 3014 being the other pair. As show, each pair of legs have a plurality of barbs 3015 on the interior surface that faces the other leg in the pair. The bone staple 3000 is comprised of a shape memory material such that the staple is movable between an insertion shape (shown in FIG. 12B) and a relaxed shape (shown in FIG. 12D).

The bone staple 3000 is not an intermedullary device and the bridge 3020 has an open-loop configuration and has a thickness T of about 0.05-0.1 inches. This thickness of the bridge 3020 allows easy removal of the staple from the repair site because it is easy to grab.

Figure 12A:
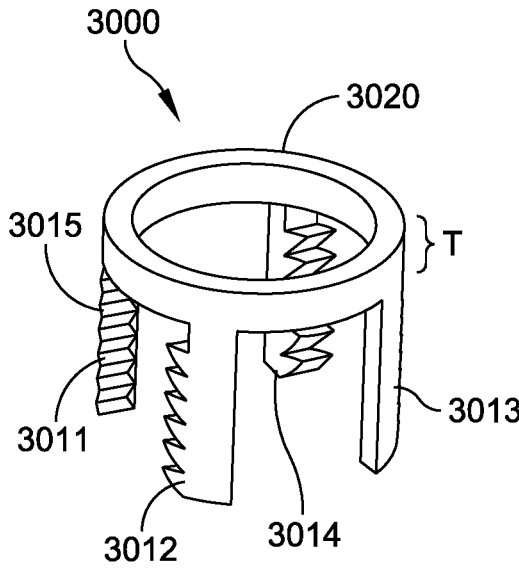
FIGS. 12A-12E are illustrations showing another shape memory metal staple according to another embodiment.

The configuration of the staple 3000 shown in FIG. 12A is its as-fabricated shape. For example, the staple 3000 can be machined out of a shape memory metal tubing (e.g. Nitinol) and retain the circular cross-sectional shape of the tube. FIG. 12C is the top down view showing the circular outline of the open-loop bridge 3020 as-fabricated from a tube.

Figure 12B:
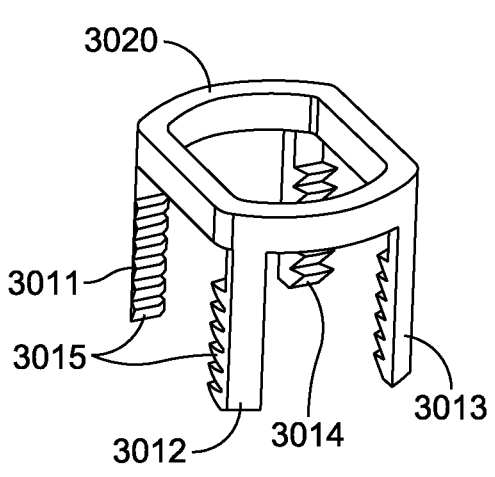
Figure 12C:
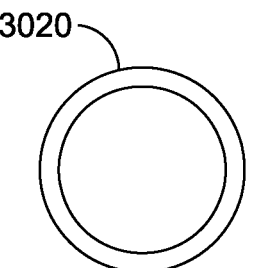
Figure 12D:
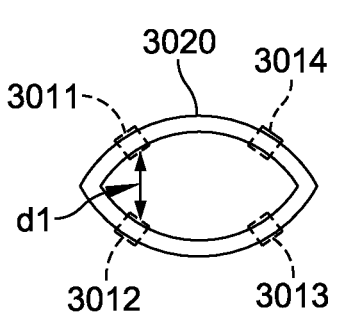

FIG. 12D shows the outline of the open-loop bridge 3020 that has been compressed into an elongated oval-like shape and heat set to set the memory metal's memorized shape. The locations of the legs 3011, 3012, 3013, and 3014 are shown by the dotted lines. The spacing between the legs of each pair of legs is set to d1.

Figure 12E:
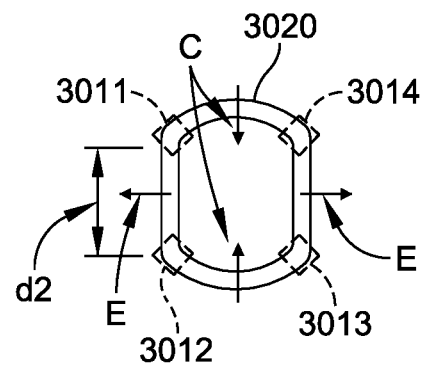

FIGS. 12B and 12E show the insertion shape of the open-loop bridge 3020 after it has been cold worked into a shape to be held by a staple holder/inserter. The configuration shown in FIGS. 12B and 12E is achieved by bending the two sections of the bridge 3020, one section between the first pair of legs 3011 and 3012, and another section between the second pair of legs 3013 and 3014, straight. The result is that the legs in each pair are moved further apart to a larger spacing d2. This configuration is the shape of the bone staple 3000 to be held by an inserting tool for implantation. Four holes are first drilled into the bone repair site using a specific drill guide for that purpose. Then, the four legs of the bone staple 3000 in the insertion shape shown in FIGS. 12B, 12E is inserted into those holes. As the bone staple 3000 reaches the activation temperature in the patient's body, the bridge 3020 of the bone staple 3000 returns to the memory set shape (i.e., the relaxed shape) shown in FIG. 12D. During this transformation, the two straight segments of the staple 3000 will move outward as indicated by the arrows E in FIG. 12E. This causes the other two segments of the bridge 3020 (the segments on top and bottom of FIG. 12E to move inward toward each other as indicated by the arrows C. This will generate compression force in the same direction as the arrows C as the legs try to return to the relaxed shape of FIG. 12D.

Referring to FIGS. 13A-13D, a bone staple 4000 having four staple legs in offset arrangements according to some other embodiments are disclosed. In these figures, the bone staple 4000 is shown in its insertion shape, as the staple legs are all shown in parallel arrangement. The bone staple 4000 comprises a bridge 4020 having an elongated shape with a longitudinal axis L defined through its length. The bridge 4020 further comprises a first corner 4021, a second corner 4022, a third corner 4023, and a fourth corner 4024. The bone staple 4000 also comprises a first leg 4011 extending from the first corner 4021, a second leg 4012 extending from the second corner 4022, a third leg 4013 extending from the third corner 4023, and a fourth leg 4014 extending from the fourth corner 4024. As shown, the first leg 4011 and the third leg 4013 are configured to be the pair providing the necessary compressive force when the staple is implanted into a bone repair site. The second leg 4012 and the fourth leg 4014 are configured to be the second pair providing the necessary compressive force when the staple is implanted into a bone repair site. As shown in FIG. 13A, the two legs that are paired for providing the compression function have a plurality of barbs 4015 on the surface that face each other. The barbs 4015 are oriented to prevent the staple from backing out once the staple is placed into a bone.

The bridge 4020 can also comprise a central reinforcement ridge 4027 that extends down the length of the bridge 4020. The central ridge 4027 is thicker than the rest of the bridge and reinforces the strength and regidity of the bridge 4020. When the thickness of the central ridge 4027 is appropriately thick, the rigidity of the bridge 4020 can be comparable to a bone plate. In some embodiments, the central ridge 4027 is the thickest near the center of the bridge 4020 and tapers to the flat portion of the bridge 4020 near the two ends of the bridge 4020 to provide a smooth profile.

The bridge 4020 comprises a first section that includes the first and second corners 4021, 4022 and a second section that includes the third and fourth corners 4023, 4024. The first and second corners 4021, 4022 are arranged such that a line L1 connecting the first and second corners 4021, 4022 intersect the longitudinal axis L of the bridge 4020 at a first non-orthogonal angle θ1.

In some embodiments of the bone staple 4000, the third and fourth corners 4023, 4024 are arranged such that a line L2 connecting the third and fourth corners 4023, 4024 intersect the longitudinal axis of the bridge at a second non-orthogonal angle θ2. In some embodiments, as shown in FIG. 13A, the first non-orthogonal angle θ1 and the second non-orthogonal angle θ2 are different. Thus, the bone staple 4000 is configured so that the first pair of staple legs 4011, 4013 have greater spacing between them compared to the second pair of staple legs 4012, 4014. The first pair of staple legs 4011, 4013 can span across a greater distance in the bone compared to the second pair of staple legs 4012, 4014. An example of use for such bone staple 4000 is for metatarsophalangeal (MTP) fusion. Having four offset legs, the bone staple 4000 can be much more robust in being useful in various situations depending on the particular arrangement and physiology of the patient. The bone staple 4000 can be fabricated to have different offset configuration to fit the needs of different situation.

In some embodiments, the first non-orthogonal angle θ1 and the second non-orthogonal angle θ2 can be the same angle. An example of such configuration is shown in the bone staple 4000A shown in FIG. 13D. In this embodiment, the first pair of staple legs 4011A, 4013A and the second pair of staple legs 4012A, 4014A have the same spacing between the legs in each pair. The two pairs are just offset from each other and parallel to the longitudinal axis L of the bridge portion 4020. Thus, the four corners 4021A, 4022A, 4023A, 4024A and their respective staple legs 4011A, 4012A, 4013A, 4014A each form a parallelogram arrangement as shown in FIG. 13D.

As shown in the embodiment of the bone staple in FIG. 13D, the line L1 connecting the first and second corners 4021A, 4022A and the line L2 connecting the third and fourth corners 4023A, 4024A can be parallel.

According to some embodiments, each of the four legs on the staple 4000, 4000A can have a length that is independent of one another as can be seen in FIG. 13B to accommodate particular anatomical locations. For example, the bone staple 4000 shown in FIG. 13B where the two legs 4011 and 4012, which are one leg in each of the two pairs, are longer than their paired legs 4013 and 4014, respectively, can be useful where one side of the bone repair/susion site has a larger bone piece than the other. The longer legs would go into the larger bone piece.

In some embodiments, all four of the staple legs on the bone staple 4000, 4000A can be of the same length.

In some embodiments, the bridge 4020 has an upper surface that curves down ward from the center line L to the four corners 4021, 4022, 4023, 4024.

Figure 6A:
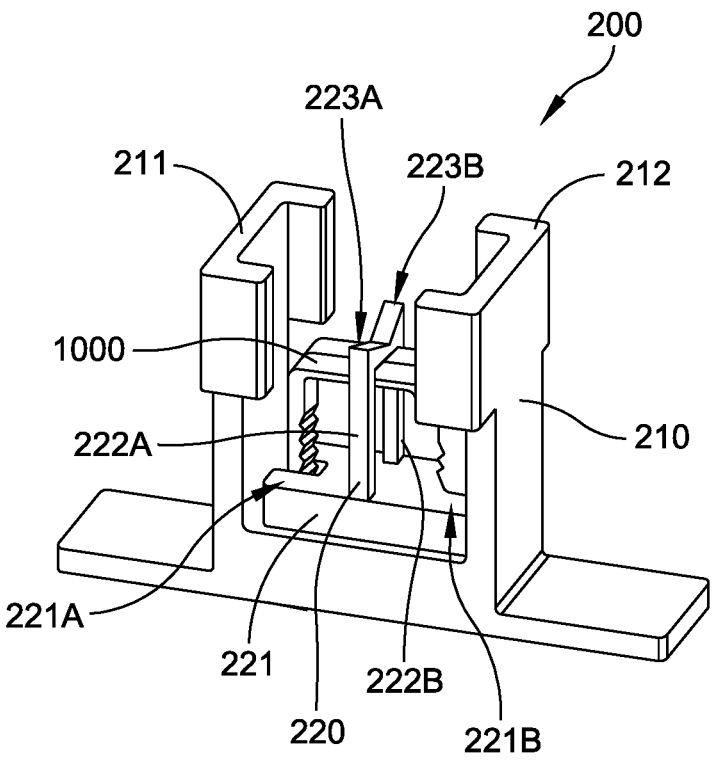
FIGS. 6A and 6B illustrate a universal staple holder for inline bone staples according to an embodiment of the present disclosure.

According to an aspect of the present disclosure, FIGS. 6A-7D show a bone staple insertion system. The bone staple insertion system comprises a staple holding cartridge 200 and a universal staple inserter 400. FIGS. 6A-6B show a cartridge 200 configured for holding a two-legged inline bone staple such as the staple 1000 (shown in FIG. 5A) that facilitates staple insertion procedure.

The cartridge 200 comprises an outer frame 210 and an inner frame 220. The inner frame 220 is configured to releasably hold a bone staple 1000 in its insertion shape. In the insertion shape, the bridge portion 1020 of the staple 1000 is straightened with the two legs 1011 and 1012 opened so that they are substantially parallel to each other.

The inner frame 220 comprises a base portion 221 and a pair of restraining arms 222A and 222B that extend upward from the base portion 221. Each of the restraining arms 222A, 222B has a restraining tab 223A, 223B, respectively, at the top end of the restraining arms 222A, 222B. The restraining tabs 223A, 223B extend inward toward each other and meet in the middle of the space between the two restraining arms 222A, 222B.

Figure 6B:
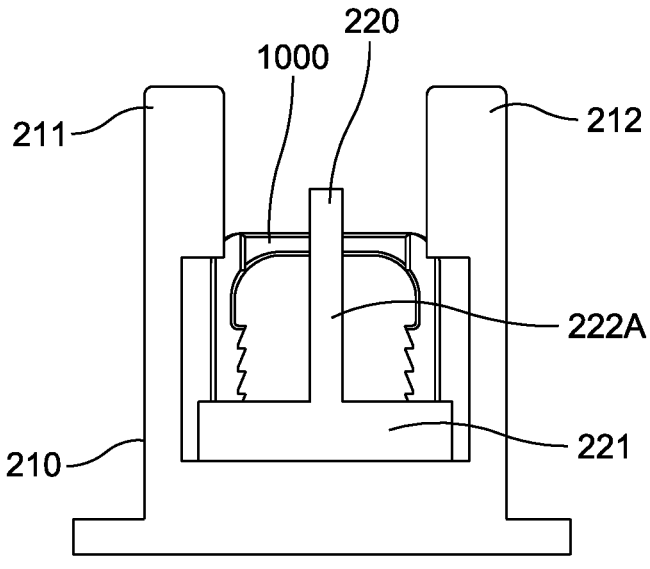

As shown in FIGS. 6A and 6B, the bone staple 1000 is loaded onto the inner frame 220 so that the two legs 1011, 0102 of the staple 1000 are held in the open configuration (i.e., the two legs substantially parallel to each other), preventing them from closing back to their relaxed position, and the bridge portion 1020 is braced against the restraining tabs 223A, 223B.

To help keep the two legs 1011, 1012 of the bone staple 1000 in the open configuration, the base portion 221 of the inner frame 220 is provided with two recesses 221A and 221B, into which the two staple legs are inserted. This can be better seen in FIG. 6A.

The two restraining tabs 223A, 223B are not permanently connected to each other so the staple 1000 can be removed from the inner frame 220 by spreading the two restraining arms 222A and 222B apart.

The base portion 210 of the cartridge 200 comprises two guiding towers 211, 212 that are spaced apart at a set distance for receiving and guiding the universal staple inserter 400. FIGS. 7A-7D show the engaging action of the cartridge 200 and the universal staple inserter 400. The universal staple inserter 400 is configured so that the staple inserter 400 and the configuration of the cartridge 200 enables transfer of the bone staple 1000 from the cartridge 200 to the universal staple inserter 400 in one single engaging motion. The engaging motion is the simple motion of inserting the universal staple inserter 400 between the two guiding towers 211, 212 straight down as represented by the downward arrow in FIG. 7A.

The universal staple inserter 400 comprises two pairs of staple grabbers 410A, 410B. Each pair of staple grabbers 410A, 410B has two arms, one on each side of the inserter 400, extending downward. The leading ends of the staple grabbers 410A, 410B have retaining tabs 411A, 411B that extend downward beyond the body of the universal staple inserter 400.

Figure 7A:
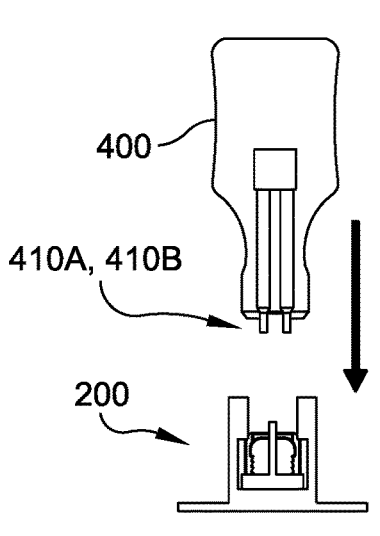
FIGS. 7A to 7D illustrate the universal bone staple holder of FIGS. 6A, 6B interacting with a universal staple inserter for inline bone staples according to an embodiment of the present disclosure.
Figure 7B:
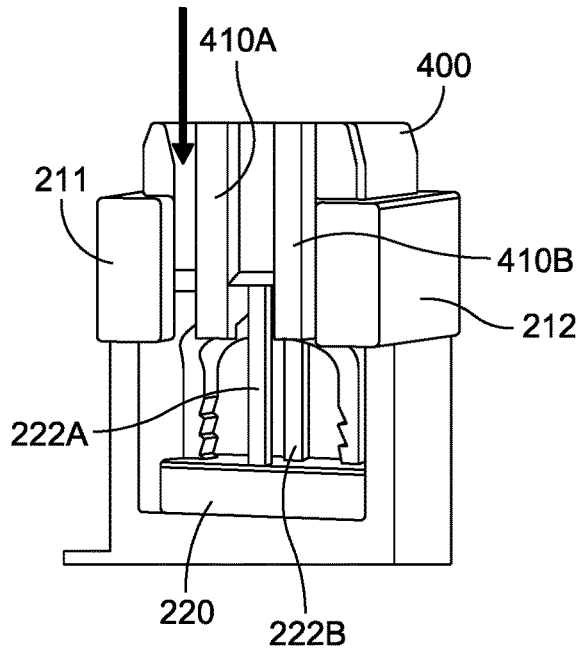
Figure 7C:
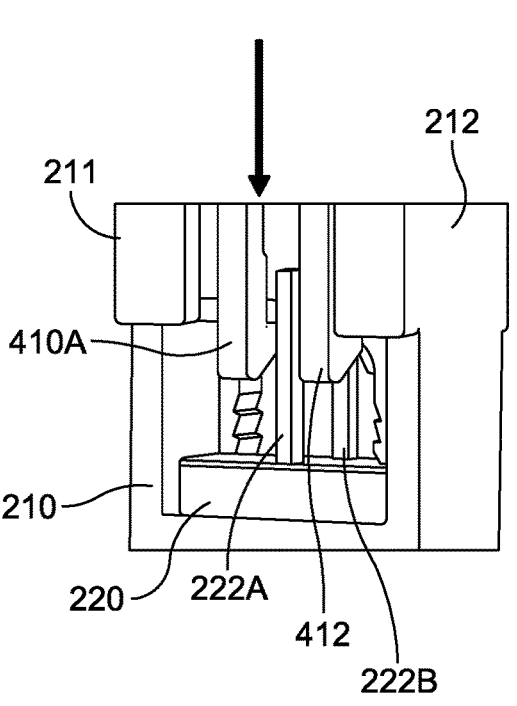

As the universal staple inserter 400 is lowered into the cartridge assembly 200 between the two guiding towers 211, 212, the retaining tabs 411A, 411B of the staple grabbers 410A, 410B encounter the bridge portion 1020 of the bone staple 1000 causing the retaining tabs 411A, 411B, and in turn the staple grabbers 410A, 410B, to spread apart. The retaining tabs 411A, 411B have a wedge-like shape as shown in FIG. 7C to facilitate this action. As the universal staple inserter 400 is pushed down further, the retaining tabs 411A, 411B slides over the bridge portion 1020 then snaps back toward their resting position so that the arms of each pair of the staple grabbers 410A, 410B close together from the opposite sides with the bridge portion 1020 of the staple 1000 caught in between. At this stage, the retaining tabs 411A, 411B are now underneath the bridge portion 1020. This position is shown in FIG. 7C. The wedge-like shape of the retaining tabs 411A, 411B helps to retain the staple 1000.

Additionally, as the universal staple inserter 400 is being lowered into the cartridge assembly 200 and the retaining tabs 411A, 411B are passing by the bridge portion 1020, the leading end of the main body of the universal staple inserter 400 gets wedged in between the two restraining tabs 223A, 223B of the inner frame 220 and urge them apart so that the restraining tabs 223A, 223B no longer are holding down the staple as the retaining tabs 411A, 411B of the staple grabbers 410A, 410B grab hold of the staple 1000.

Figure 7D:
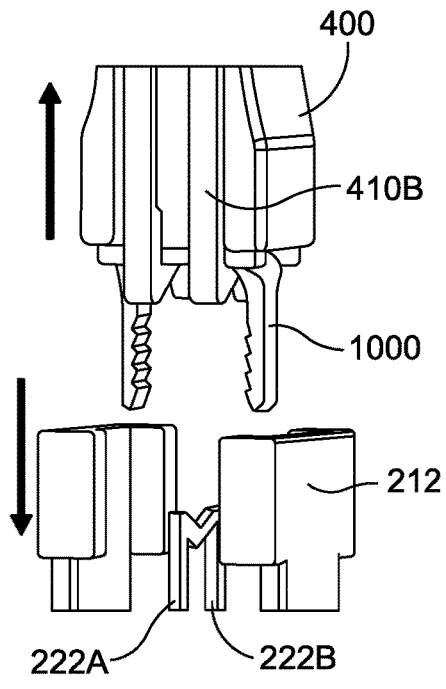

With the transfer of the staple 1000 from the inner frame 210 of the cartridge 200 to the universal staple inserter 400 complete, the inserter 400 can now be removed from the cartridge assembly 200 as shown in FIG. 7D. The universal staple inserter 400 is now holding the staple 1000. The retaining tabs 411A, 411B of the staple grabbers 410A, 410B keep the bridge portion 1020 of the staple 1000, which is normally bowed upward in the relaxed shape as shown in FIG. 5A, substantially straight as shown. This maintains the staple 1000 in its insertion shape with its two legs in substantially parallel configuration so that the staple can be inserted into a bone repair site. The universal staple inserter 400 is configured so that the two pairs of staple grabbers 410A, 410B can be quickly spread apart and release the staple after the staple has been inserted into a bone repair site.

The cartridge assembly 200 and the associated universal staple inserter 400 allows one staple inserter to be universally used with staples of a variety of sizes. As long as the central portions of the bridge portion 1020 of the staples of varying sizes are configured to have the same bowed shape, the universal staple inserter 400 can be used in conjunction with the cartridge assembly 200 holding each of the staples. The cartridge assembly 200 would be provided in different sizes to hold different size staples. The two guiding towers 211, 212 of the cartridge assemblies 200 will all be the same size to receive the universal staple holder 400.

Figure 8:
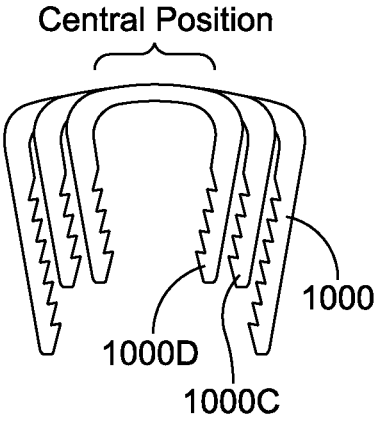
FIG. 8 is an illustration of an overlapping view of three different size staples that are configured for using with the universal staple holder shown in FIGS. 6A and 6B.

FIG. 8 is an illustration of an overlapping view of three different size staples 1000, 1000C, and 1000D that are configured for using with the universal staple inserter 400. The bridge portions of the three staples have a Central Portion that have the same bowed shape.

Referring to FIGS. 14A-14I, a bone staple inserter system according to another embodiment is disclosed. The bone staple inserter system comprises a cartridge 777 shown in FIG. 14A. A bone staple such as the two-legged inline staple 1000 shown in FIG. 5A is securely mounted to the cartridge 777. As described above, the bone staple 1000 comprises a first leg and a second leg oriented toward each other in a relaxed state, and a curved bridge portion 1020 connecting the first and second legs, where the cartridge 777 comprises a first end and a second end, the first end provided with a channel 710 that is sized to receive the bridge portion 1020 of the bone staple 1000 and securely hold the bone staple 1000 by an interference fit.

The bone staple inserter system also comprises a bone staple inserter 700A that is configured to receive the cartridge 777.

Figure 14A:
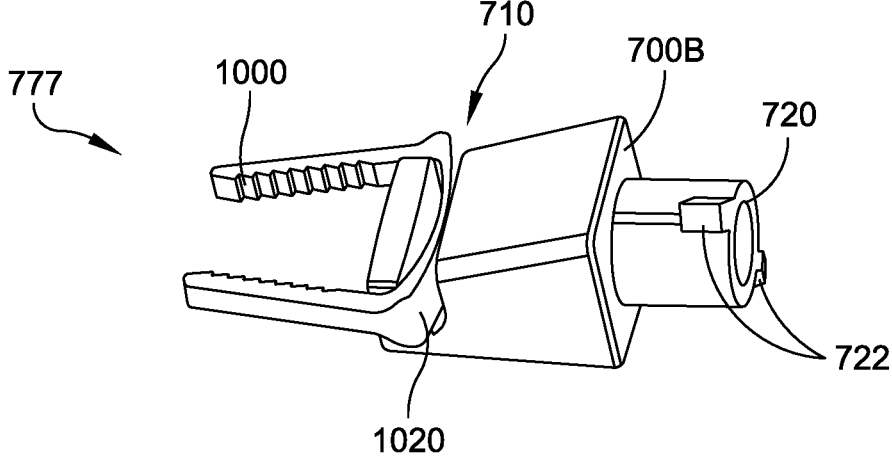
FIGS. 14A-14I are illustrations showing a universal staple inserter system of the present disclosure.

Referring to FIG. 14A, the cartridge 777 also comprises a connector part 720 that is configured to securely attach to the bone staple inserter 700A. In the illustrated example, the connector part 720 is a cylindrical structure and comprises two tabs 722 configured for releasably attaching to the bone staple inserter 700A by a twisting motion.

Figure 14B:
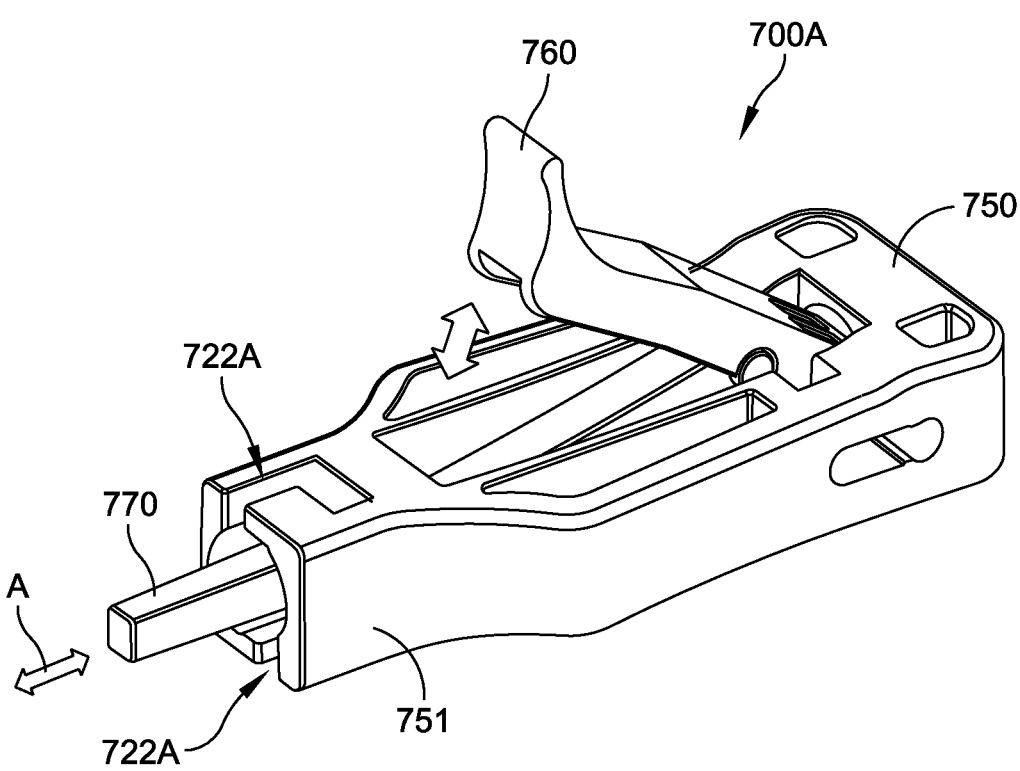
Figure 14C:
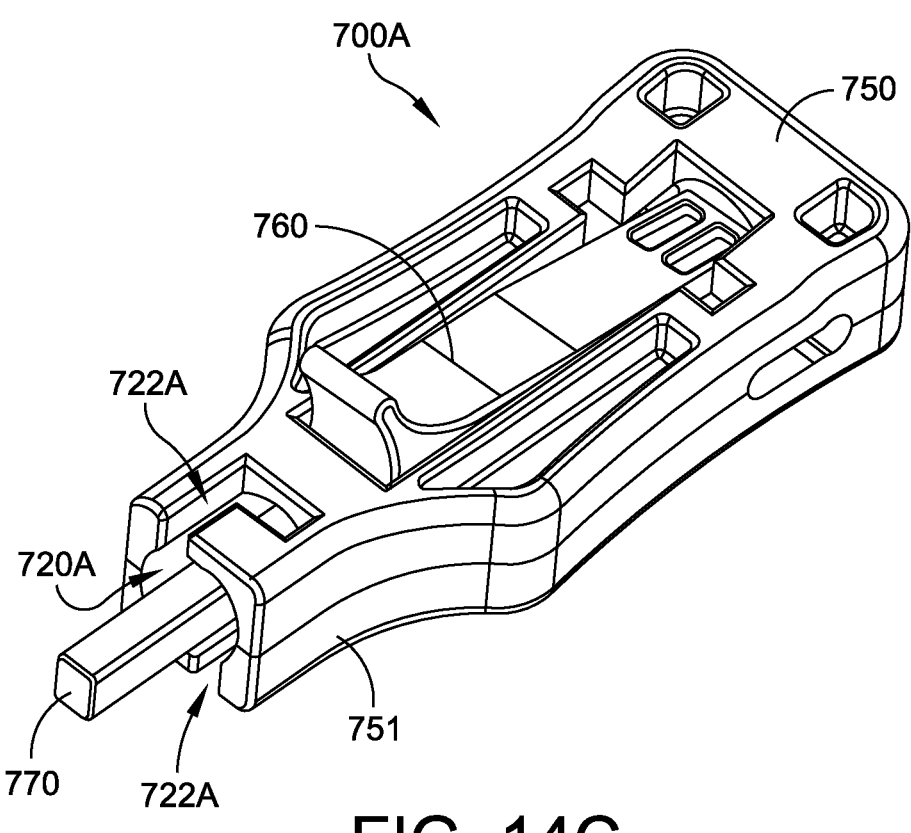
Figure 14D:
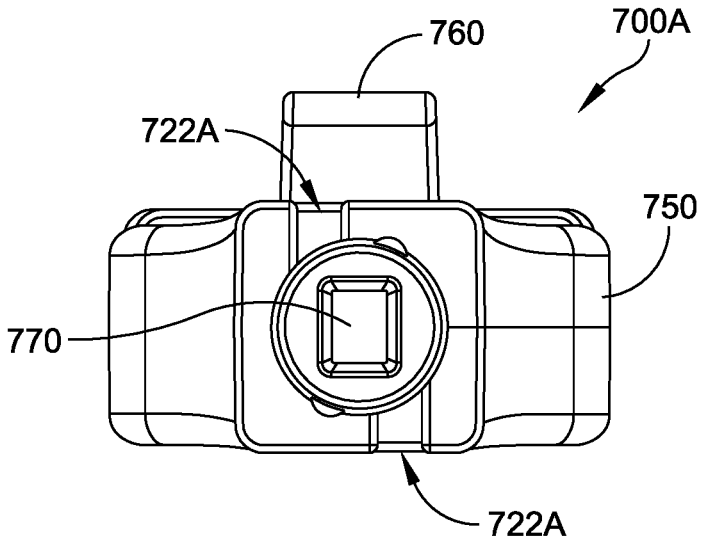

Referring to FIGS. 14B-14D, the bone staple inserter 700A has a body 750. The body has a cartridge engaging end 751 that is configured with a recess 720A for receiving the connector part 720 of the cartridge. Around the periphery of the recess 720A is provided with two L-shaped cutouts 722A for receiving the two tabs 722 on the connector part 720 of the cartridge 777. The L-shape of the cutouts 722A allows the tabs 722 to first engage the cartridge engaging end 751 straight then twisted to temporarily lock the cartridge 777 with the inserter 700A.

The inserter 700A further comprises a pushrod 770 that protrudes through the recess 720A for engaging the cartridge 777 and release the staple 1000 from the cartridge 777. The pushrod 770 is configured to move in and out of the cartridge engaging end 751 as indicated by the arrow A in FIG. 14B. The movement of the pushrod 770 is controlled by a lever 760. The lever 760 is connected to the pushrod 770 on the opposite end of the pushrod 770 by a hinged connection so that when the lever 760 is pulled up as shown in FIG. 14B, the pushrod 770 is in its retracted position. When the lever 760 is pushed down into the body 750 as shown in FIG. 14C, the pushrod 770 is in its fully extended position.

Figure 14E:
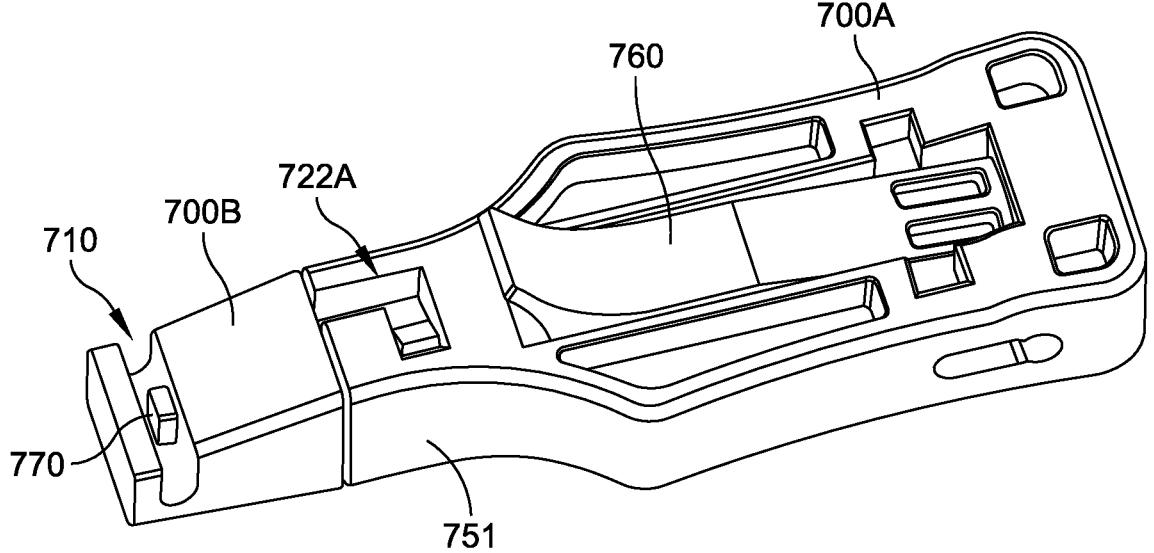
Figure 14F:
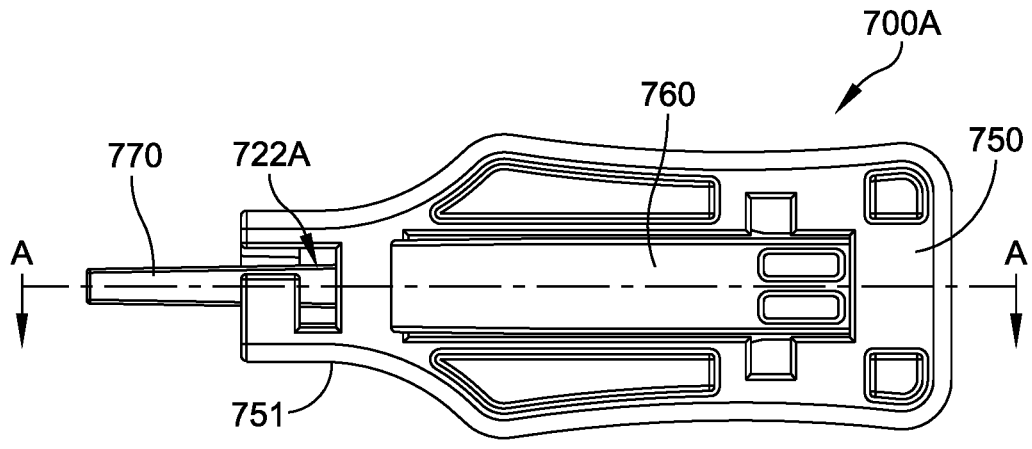
Figure 14G:
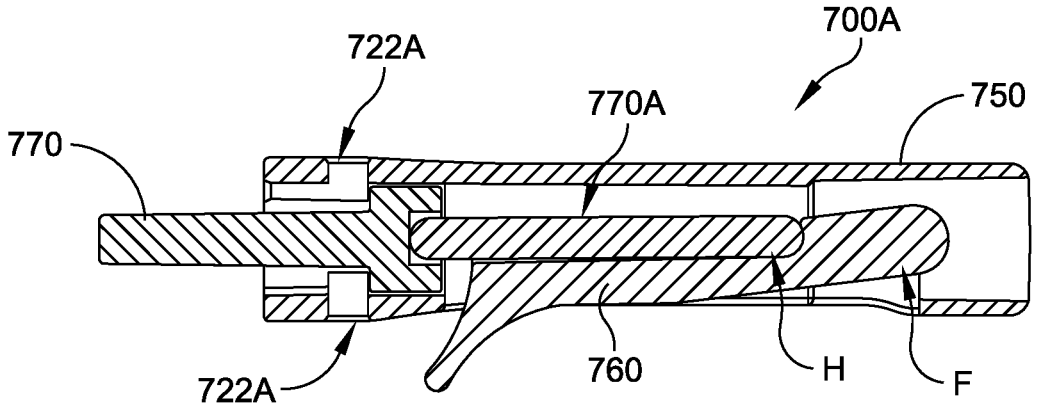
Figure 14H:
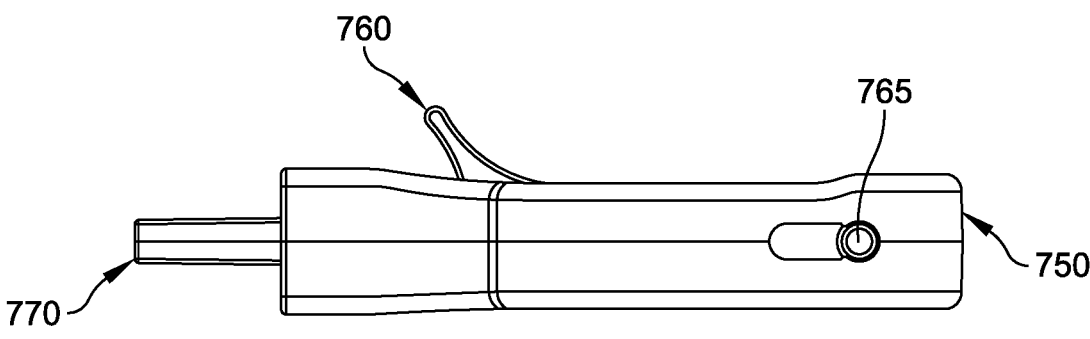
Figure 14I:
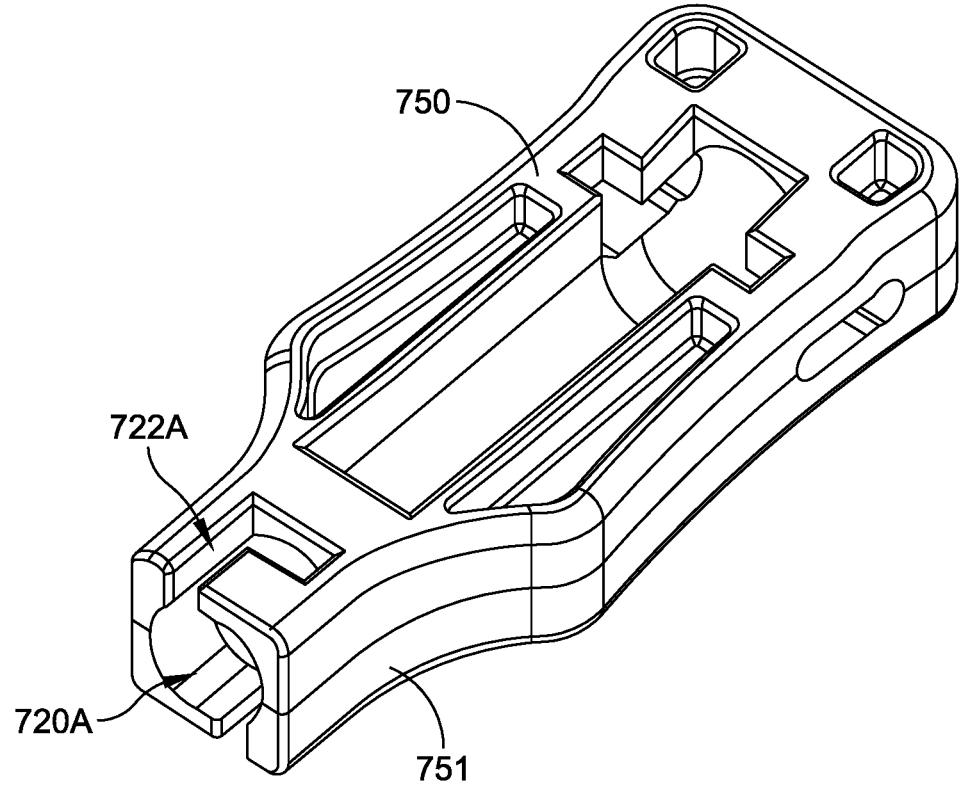

An exemplary mechanical arrangement that enables the reciprocating motion of the pushrod 770 by the manipulation of the lever 760 is shown in the cross-sectional view of the staple inserter 700A shown in FIG. 14G. In this example, the pushrod 770 is connected to the lever 760 via an intermediate linkage 770A. The connections between the intermediate linkage 770A and the pushrod 770 and the lever 760 are both hinged connections to accommodate the angular bending at those connection points when the lever 760 goes from the pushed-down position of FIG. 14 G to the pulled-up position of FIG. 14B. The lever 760 is connected to the body 750 by a hinge pin 765 as shown in the side view of FIG. 14H. The hinge pin 765 defines the fulcrum F (shown in FIG. 14G) and provides the hinged movement for the lever 760. The hinged connection between the intermediate linkage 770A and the lever 760 is identified by the point H in FIG. 14G. Because the hinge point H is between the pushrod 770 and the fulcrum F, when the lever 760 is pulled up, the hinge point H rises with the lever 760 and the intermediate linkage 770A pulls the pushrod 770 into the body 750 into its retracted position. When the lever 760 is pushed back down, the reverse happens and the intermediate linkage 770A pushes the pushrod 770 out to its extended position.

Referring to FIG. 14E which shows the empty cartridge 700B attached to the inserter 700A, the pushrod 770 in its fully extended position can be seen. In this position, the pushrod protrudes into the channel 710. Thus, when a bone staple 1000 is securely loaded into the channel 710 by a press-fitting or an interference-fitting, the bowed portion of the staple's bridge 1020 sits within the channel 710. In use, the lever 760 on the staple inserter 700A is first pulled up to full retract the pushrod 770. Then, the connector part 720 of a loaded cartridge 700B is inserted into the recess 720A of the staple inserter 700A and twisted to lock the engagement. At this point, the staple 1000 is in its relaxed shape and the two legs of the bone staple 1000 are biased toward each other as shown in FIG. 14A. Next, the staple 1000 is changed into its insertion shape by pushing the lever 760 down to the position shown in FIGS. 14C and 14E. This extends the pushrod 770 into the channel 710 which pushes on the bridge 1020 of the staple 1000 from the convex side of the bowed bridge 1020. This straightens the bridge 1020 causing the two legs of the staple 1000 to be substantially parallel to each other. With the staple 1000 engaged with the inserter 700A in this manner and the lever 760 is in the down position, the angle of the intermediate linkage 770A creates an over center connection where the staple pushing back on the pushrod 770 keeps the linkage formed by the pushrod 770, the intermediate linkage 770A, and the lever 760 rigid (similar to a person locking a straightened elbow) and keeps the system engaged and prevents the lever from popping up to the pulled up position when not desired. Now, the staple 1000 is in its insertion shape and the surgeon can insert the staple 1000 into the pre-drilled holes in the bone repair site. After the insertion, the inserter 700A/cartridge 700B assembly can be removed by pulling up on the lever 760 to retract the pushrod 770 and relieve the pressure on the bridge 1020 returning the staple 1000 to its relaxed shape. Because the staple 1000 is now held only by the friction between the channel 710 in the cartridge 700B and the bridge 1020, the inserter 700A/cartridge 700B assembly can be removed by laterally twisting the assembly.

Method of Removing the Orthopedic Staple

According to another aspect of the present disclosure, the inserter 700A and the cartridge 700B can be used to remove an orthopedic staple such as the two-legged inline staple

1000 that is implanted in a bone repair site in its relaxed state. Such method to remove an orthopedic staple that is implanted in a bone repair site in its relaxed state, wherein the orthopedic staple comprises a first leg and a second leg connected by a curved bridge portion having two ends, wherein each of the two ends of the bridge portion transition down to the first leg and the second leg, respectively, Such method comprises (a) attaching an inserter tool/cartridge assembly 700A/700B (see FIG. 14E) to the orthopedic staple's bridge portion 1020; (b) actuating the inserter tool 700A to change the orthopedic staple from its relaxed state to its insertion state in which the two legs 1011, 1012 of the orthopedic staple 1000 are substantially parallel to each other; and (c) removing the orthopedic staple 1000 from the bone repair site.

Because the inserter tool/cartridge assembly 700A/700B comprises a channel 710 that is sized to receive the curved bridge portion 1020 of the orthopedic staple 1000 and hold the orthopedic staple by an interference fit, the step (a) includes engaging the channel 710 to the curved bridge portion 1020 so that the curved bridge portion is positioned within the channel. The step (b) comprises actuating the lever mechanism 760 of the inserter tool 700A to extend the pushrod 770 into the channel 710 and engage the curved bridge portion 1020 to change the orthopedic staple 1000 from its relaxed state back to its insertion state.

In some embodiments, the method to remove the orthopedic staple 1000 can further include inserting a flat blade-like tool between the orthopedic staple's bridge portion 1020 and the bone surface of the bone repair site and lifting the orthopedic staple's bridge portion away from the bone surface, creating a space between the orthopedic staple's bridge portion and the bone surface, before the step (a).

According to another embodiment, a second method to remove the orthopedic staple 1000 is provided. This second method comprises: (a) attaching the cartridge 700B to the orthopedic staple's bridge portion 1020 by engaging the channel 710 of the cartridge 700B to the curved bridge portion 1020 so that the curved bridge portion is positioned within the channel; (b) attaching the inserter tool 700A to the cartridge 700B; (c) actuating the inserter tool 700A to change the orthopedic staple 1000 from its relaxed state to its insertion state in which the two legs 1011, 1012 of the orthopedic staple are substantially parallel to each other; and (d) removing the orthopedic staple from the bone repair site. The step (c) comprises actuating the lever mechanism 760 of the inserter tool 700A to extend the pushrod 770 into the channel 710 and engage the curved bridge portion 1020 to change the orthopedic staple 1000 from its relaxed state back to its insertion state.

The second method to remove the orthopedic staple 1000 can further comprise inserting a flat blade-like tool between the orthopedic staple's bridge portion 1020 and the bone surface of the bone repair site and lifting the orthopedic staple's bridge portion away from the bone surface, creating a space between the orthopedic staple's bridge portion and the bone surface, before the step (a).

Figure 9:
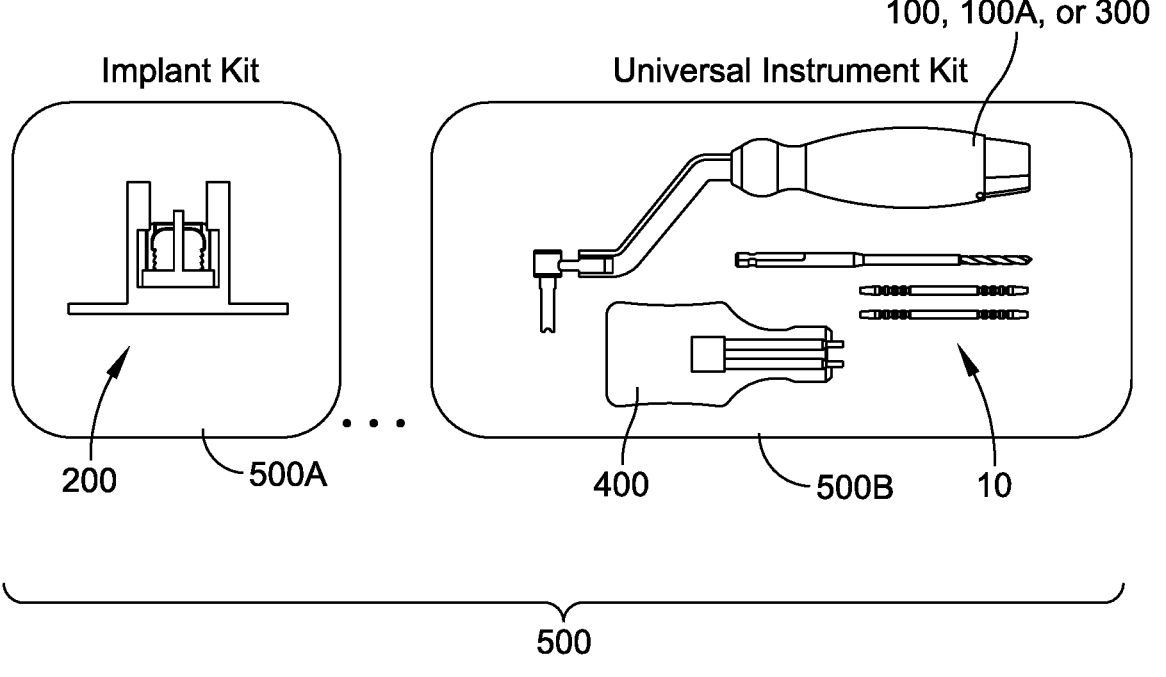
FIG. 9 shows in combination show a surgical kit providing inline bone staples in the universal staple holders shown in FIG. 6A and the associated universal instruments: the orthopedic drill guide shown in FIG. 4A; and a universal staple inserter shown in FIG. 7A.

Referring to FIG. 9, according to an aspect of the present disclosure, a bone staple inserter kit 500 for implanting two-legged inline bone staples such as those illustrated in FIGS. 5A-5E is disclosed. The bone staple inserter kit 500 comprises a first sterile package 500A containing a first bone staple securely mounted to a first cartridge assembly 200 described above. The first bone staple comprises a first leg and a second leg oriented toward each other in a relaxed state, and a curved bridge portion connecting the first and second legs.

The bone staple inserter kit 500 also comprises second sterile package 500B containing a bone staple inserter 400 described above that is configured to receive the cartridge assembly 200 loaded with a bone staple. The second sterile package 500B also contains a universal drill guide assembly (like the drill guide assemblies 100, 100A, or 300). The second sterile package 500B can also contain other hardware components 10 necessary to use the drill guide. Some examples are one or more drill bits, fixation pins, etc.

In some embodiments, the bone staple inserter kit 500 can further comprise one or more additional sterile packages, like the sterile package 500A, each containing an additional cartridge assembly securely holding a bone staple, where the bone staples in the additional sterile packages can be of same or difference size as the bone staple in the first sterile package.

By providing bone staple inserter kits such as 500 described herein, only one set of universal instruments need to be provided in one sterile package 500B and several different sterile packages 500A each containing a different size staple can be provided.

Figure 15:
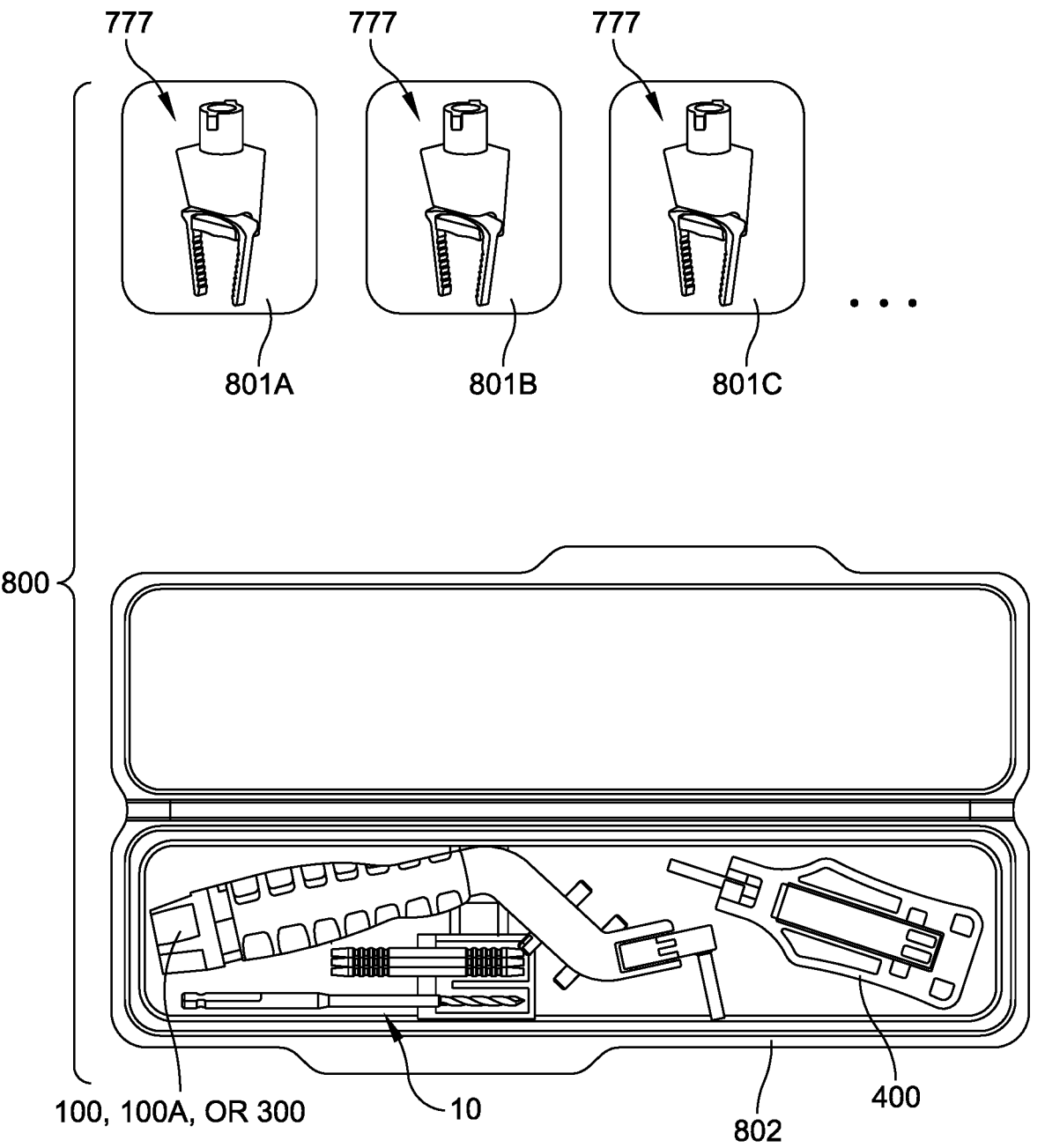
FIG. 15 is an illustration of a surgical kit according to the present disclosure.

Referring to FIG. 15, according to an aspect of the present disclosure, a bone staple inserter kit 800 is disclosed. Such kit comprises a first sterile package 801A containing a cartridge assembly 777 and a second sterile package 802 containing a set of universal instruments needed for implanting bone staples.

The cartridge assembly 777 provided in the first sterile package 801A comprises a bone staple securely mounted to the first cartridge as described herein with reference to FIG. 14A. The universal instruments provided in the second sterile package 802 can comprise the staple inserter 700A described with reference to FIG. 14B. The second sterile package 802 preferably also comprises one or more of the universal drill guide 100, 100A, and 300 described herein.

In some embodiments, the bone staple inserter kit 800 can further comprise one or more additional first sterile packages 801B, 801C, etc. Each of these additional first sterile packages can contain a cartridge assembly holding a staple of different size or a same size as the staple in the first sterile package 801A.

Although the devices, kits, systems, and methods have been described in terms of exemplary embodiments, they are not limited thereto. Rather, the appended claims should be construed broadly, to include other variants and embodiments of the devices, kits, systems, and methods, which may be made by those skilled in the art without departing from the scope and range of equivalents of the devices, kits, systems, and methods.

We claim:

1. A bone staple inserter kit comprising:
a first sterile package containing a first bone staple securely mounted to a first cartridge, wherein the first bone staple includes a first leg, a second leg, and a bridge portion connecting the two legs, the bridge comprising a flat top surface along a length of the bridge portion where the flat top surface forms a convex portion that is spaced-away and laterally off-set from each of the first leg and the second leg and, having a first end opposite a spaced-away second end, and two chamfered edge surfaces that extend substantially the length of the bridge portion, the flat top surface positioned between the two chamfered edge surfaces,
wherein the flat top surface extends substantially the length of the bridge portion, so that the bridge portion defines a uniform cross-section,
wherein each of the first end of the bridge portion transitions down to the first leg and the second end of the bridge portion transitions down to the second leg, and the first cartridge comprises a first end and a second end, the first end provided with a channel that is sized to receive the bridge portion of the first bone staple and securely hold the first bone staple by an interference fit; and
a second sterile package containing: a bone staple insertion tool that is configured to receive a cartridge, like the first cartridge that has a bone staple, like the first bone staple, securely mounted thereon; a universal drill guide assembly; and a drill bit, wherein the bone staple insertion tool comprises a lever and a pushrod that can transform the bone staple to an insertion shape after the cartridge with the bone staple mounted thereon is mounted on the insertion tool; and wherein the lever is operatively linked to the pushrod such that actuation of the lever directly causes linear movement of the pushrod so as to engage the convex portion of the bone staple.

2. The bone staple inserter kit of claim 1, wherein each of the first and second legs comprises an inner surface defining a plurality of barbs, wherein each of the plurality of barbs comprises a tip located at least one of flush with and below the inner surface of the legs.

3. The bone staple inserter kit of claim 1, wherein each of the first and second legs comprises a proximal end and a distal end and each distal end includes a wedge-shaped tip.

4. The bone staple inserter kit of claim 1, wherein the flat top surface has a width that is greater than its thickness.

5. The bone staple inserter kit of claim 1, wherein the staple is comprised of a shape memory material such that the staple is movable between an insertion shape and a relaxed shape.

6. The bone staple inserter kit of claim 1, wherein a ratio of the width/thickness is about 2.0 to 2.5.

7. The bone staple inserter kit of claim 1, wherein the pushrod applies pressure on the bridge portion of the staple to straighten the curved bridge portion after the cartridge that has the bone staple is mounted on the insertion tool, wherein straightening a curved bridge portion expands the first and second legs of the bone staple into the insertion shape.

8. The bone staple inserter kit of claim 1, further comprising a third sterile package containing a second bone staple securely mounted to a second cartridge, wherein the second bone staple comprises a first leg and a second leg oriented toward each other in a relaxed state, and a curved bridge portion connecting the first and second legs, wherein the second cartridge comprises a first end and a second end, the first end provided with a channel that is sized to receive the bridge portion of the second bone staple and securely hold the second bone staple by an interference fit, wherein the first bone staple and the second bone staple have different sizes.

* * * * *